United States Patent [19]

Sasaki et al.

[11] Patent Number: 5,374,953
[45] Date of Patent: Dec. 20, 1994

[54] ELECTRONIC ENDOSCOPE APPARATUS WITH SIGNAL VALIDITY MONITOR

[75] Inventors: Masahiko Sasaki; Masao Uehara, both of Hachioji; Katsuyuki Saito, Kokubunji; Akinobu Uchikubo, Ome; Shinji Yamashita, Hachioji; Takehiro Nakagawa, Hachioji; Akihiro Miyashita, Hachioji; Masahide Kanno, Hachioji; Katsuyoshi Sasagawa, Hino; Jun Hasegawa, Hachioji, all of Japan

[73] Assignee: Olympus Optical Co., Ltd., Tokyo, Japan

[21] Appl. No.: 82,508

[22] Filed: Jun. 25, 1993

Related U.S. Application Data

[63] Continuation of Ser. No. 783,947, Oct. 28, 1991, abandoned.

[30] Foreign Application Priority Data

Feb. 1, 1991 [JP] Japan .................. 3-012199
Sep. 26, 1991 [JP] Japan .................. 3-247770

[51] Int. Cl.⁵ .................. A61B 1/04; A61B 1/06
[52] U.S. Cl. .................. 348/65
[58] Field of Search .......... 358/98, 213.23, 213.29, 358/88, 91; 128/6; 348/65, 68, 69, 70, 71, 74

[56] References Cited

U.S. PATENT DOCUMENTS

| | | | |
|---|---|---|---|
| 4,193,093 | 3/1980 | St. Clair | 358/213.23 |
| 4,535,758 | 8/1985 | Longacre | 128/6 |
| 4,613,899 | 9/1986 | Kuwano | 358/91 |
| 4,646,724 | 3/1987 | Sato | 358/98 |
| 4,699,125 | 10/1987 | Komatsu | 358/98 |
| 4,734,756 | 3/1988 | Butterfield | 358/91 |
| 4,757,386 | 7/1988 | Sanner . | |
| 4,797,737 | 1/1989 | Yazawa | 358/98 |
| 4,860,095 | 8/1989 | Kimura | 358/98 |
| 4,928,172 | 5/1990 | Uehara | 358/98 |
| 4,951,135 | 8/1990 | Sasagawa | 358/98 |
| 4,963,960 | 10/1990 | Takami | 358/98 |
| 5,049,989 | 9/1991 | Tsuji | 358/98 |
| 5,113,254 | 5/1992 | Kanno | 358/98 |
| 5,131,381 | 7/1992 | Ams | 128/6 |

FOREIGN PATENT DOCUMENTS

61-61588 3/1986 Japan .

*Primary Examiner*—Tommy P. Chin
*Assistant Examiner*—Bryan S. Tung
*Attorney, Agent, or Firm*—Armstrong, Westerman, Hattori, McLeland & Naughton

[57] ABSTRACT

In an electronic endoscope apparatus each of the signals of a plurality of systems output from at least one solid state imaging device is judged by a signal monitoring device as to whether it is normal or not. On the basis of the judged result, the processing mode corresponding to each of the signals of the plurality of systems is changed and each signal is processed. If an abnormality occurs, an observed image with which the endoscope inspection can continue will be secured to be safe. Further, in the electronic endoscope apparatus, when the output signal from the solid state imaging device is judged to be abnormal, the amount of illuminating light will be attenuated, the danger by the excessive amount of illuminating light will be avoided and the safety of the person being monitored will be secured.

4 Claims, 21 Drawing Sheets

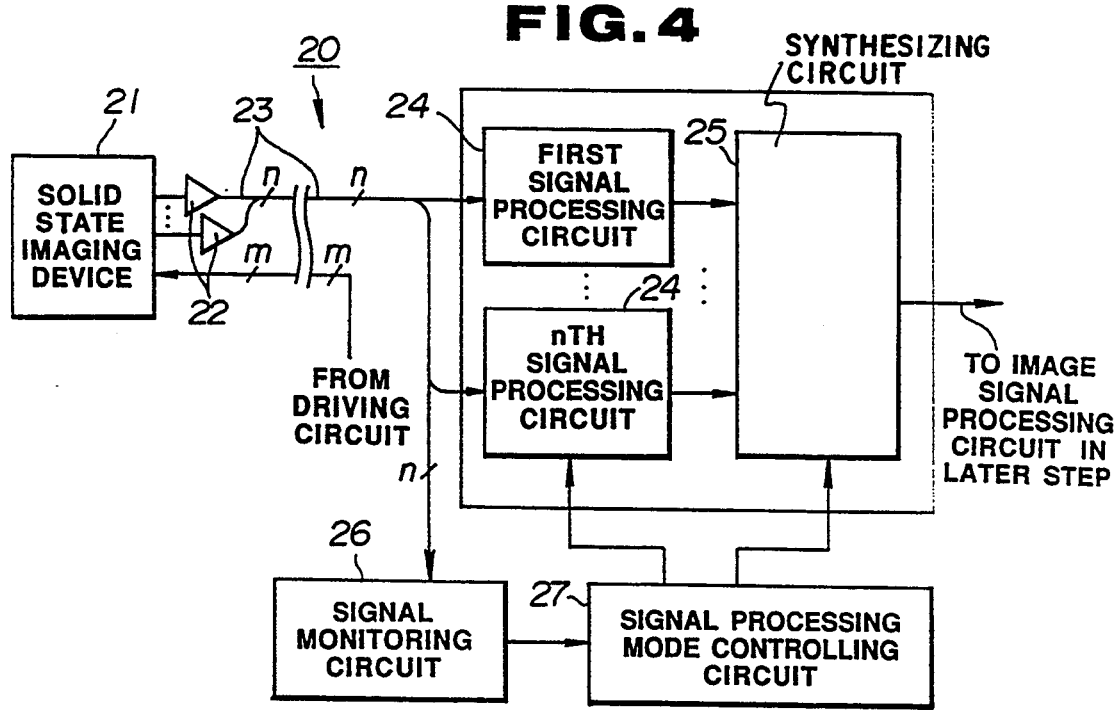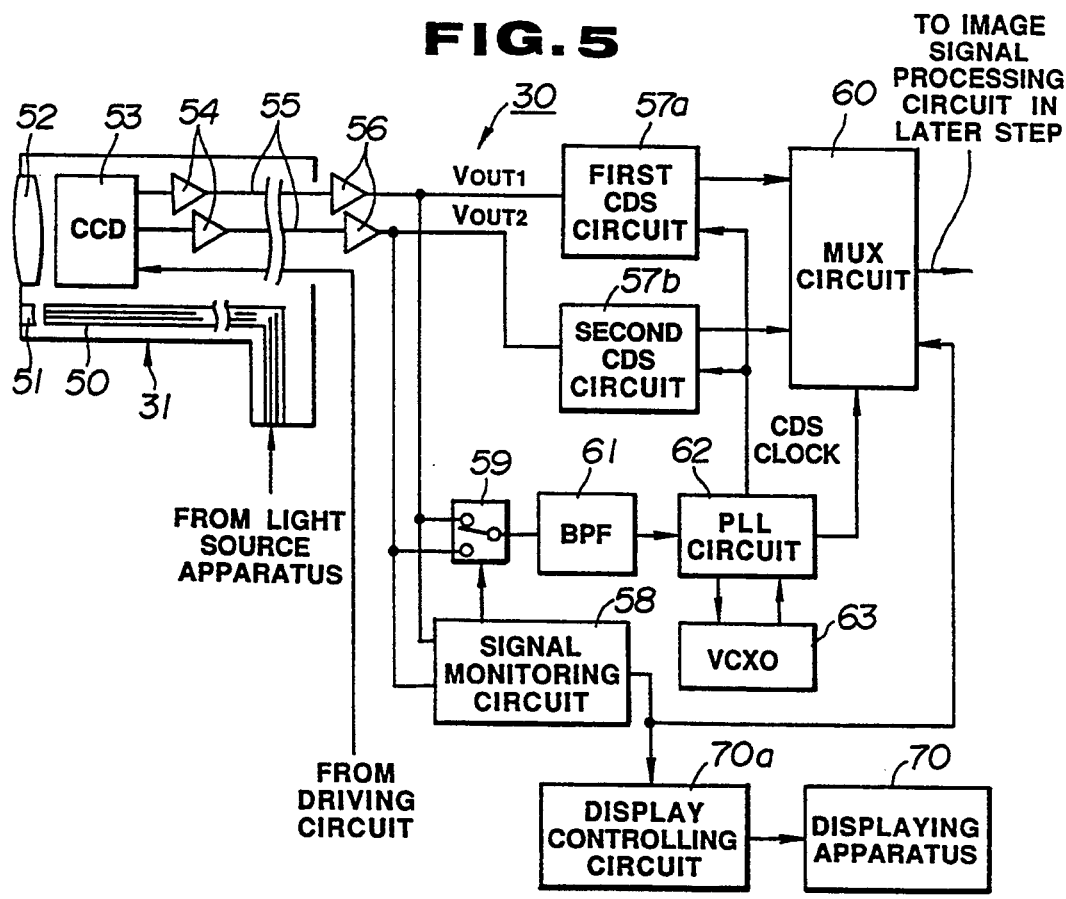

ELECTRONIC ENDOSCOPE APPARATUS WITH SIGNAL VALIDITY MONITOR

This application is a continuation of application Ser. No. 07/783,947 filed Oct. 28, 1991, now abandoned.

BACKGROUND OF THE INVENTION

1. Field of the Invention

This invention relates to an electronic endoscope apparatus wherein signals of a plurality of systems output from at least one solid state imaging device are monitored and the safety in case an abnormality occurs is improved.

2. Description of the Related Art

Recently there is extensively utilized an endoscope whereby organs within a body cavity or the like can be observed by inserting an elongated insertable part into the body cavity or various therapeutic treatments can be made by using treating instruments inserted through treating instrument channels as required. Such endoscopes are used not only for therapeutic uses but also for industrial uses to observe and inspect such objects as the interiors of boilers, machines and chemical plant pipes.

Among the above mentioned endoscopes, there are not only optical endoscopes (so called fiber scopes) but also electronic endoscopes. In such an electronic endoscope, such a solid state imaging device such as a charge coupled device (CCD) is arranged in the tip part of an insertable part so that the image of an imaged object may displayed on a monitor, thereby providing a high resolution image which can be easily recorded and reproduced.

Therefore, recently, in an optical endoscope, an externally fitted camera having a solid state imaging device built-in is fitted to the eyepiece part and is used as an imaging means in many cases.

Now, as the above mentioned solid state device contains a greater number of pixels, various systems for reading out such pixel information at a high speed within a predetermined time have been devised.

For example, U.S. Pat. No. 4,757,386 discloses a circuit in which a CCD having two outputs is used. In this example, the outputs of two systems from the CCD have the carrier removed by a low pass filter (LPF) without using a correlated double sampling (CDS) circuit, and the dispersion of the two systems is corrected by an automatic gain circuit (AGC) provided on the rear step side. The outputs of the two systems from the CCD are then synthesized into one system by a multiplexer and are output.

However, in the above mentioned example, as the LPF is used to remove the carrier contained in the output of the CCD, the 1/f noise contained in the same output cannot be removed and an image high in the S/N ratio cannot be obtained.

As an improvement in this area, there is an electronic endoscope apparatus 1 shown in FIG. 1 and using a CCD 2 shown in FIGS. 2 and 3. The CCD 2 shown in FIGS. 2 and 3 is a line transfer type CCD provided with horizontal transfer registers in two steps. In this CCD 2, the pixel information for one scanning line transferred in each horizontal period from an imaging part 3 formed of a two-dimensional array of a photoelectric converting device is allotted to two horizontal registers 4 for each pixel and their outputs $V_{out1}$ and $V_{out2}$ are simultaneously read out through amplifiers 5. Therefore, with this CCD 2, the pixel information can be read out at a speed twice as high without increasing the frequency of the horizontal transfer clock.

As shown in FIG. 1, the electronic endoscope apparatus 1 uses the above mentioned CCD 2, and the CCD reading signals of the two systems are input respectively into the first and second correlated double sampling (CDS) circuits 9 respectively through buffers 6, coaxial cables 7 and amplifiers 8. The amplified CCD reading signals are sampled/held (S/H) by these CDS circuits 9, are then synthesized into one system by a multiplexer (MUX) circuit 10 and are sent as an imaging signal to a signal processing circuit in the later step.

On the other hand, a band pass filter (BPF) 11 inputs one of the CCD reading signals and extracts a carrier clock, and a PLL (Phase Locked Loop) circuit 12 and voltage controlled crystal oscillator (VCXO) 13 produce a CDS clock synchronized in the phase with a carrier clock of the CCD reading signal. The above mentioned PLL circuit 12 feeds the produced CDS clock to the above mentioned CDS circuits 9 and MUX circuit 10.

In this electronic endoscope apparatus 1, as the CCD synchronizing type CDS circuits 9 are adopted, a stable sampling can be attained without resorting to the lengths of the coaxial cables 7 and, as a result, the 1/f noise is greatly improved. The reference numeral 14 represents an electronic endoscope, 15 represents an objective optical system provided in the tip part of the electronic endoscope and 16 represents a light guide fiber bundle for leading an illuminating light from a light source apparatus to the above mentioned tip part side.

Now, in the electronic endoscope, as the solid state imaging device is provided near the bent part and such signal transmitting cable as the coaxial cable is inserted through a flexible tube of the electronic endoscope, it is necessary to consider countermeasures for the break of the signal transmitting cable, the break of the connecting point of the signal transmitting cable and solid state imaging device or the contact failure of the connector caused by repeating bending to convert the visual field or to insert the insertable part during the inspection with the endoscope.

Further, some electronic endoscope or externally fitted camera is provided with a plurality of solid state imaging devices in response to the difference of the observing light radiated to the object or of the imaging system. Even in such imaging means having a plurality of solid state imaging devices, it is necessary to consider the countermeasures for the break of the signal transmitting cables of a plurality of systems, the break of the connecting point of the signal transmitting cable and solid state imaging device or the contact failure of the connector and it is also necessary to consider the countermeasures for the deterioration and break of the solid state imaging device.

In such electronic endoscope apparatus as is shown in FIG. 1 for coping with them, as described above, the image information of the CCD is read out at a high speed within a predetermined time, further, the CCD read out signal synchronizing type CDS circuit is adopted, the stable sampling is attained irrespective of the length of the coaxial cable and, as a result, the 1/f noise is greatly improved. However, in case one system on the CDS clock extracting side of the two systems breaks and this CCD reading signal is no longer fed or in case the signal level becomes abnormally low, the sampling will not be able to be made in the CDS circuit.

As a result, there will be defects in that the image will be less than whole and no normal endoscope inspection will be made.

Also, during the inspection with the electronic endoscope having a plurality of solid state imaging devices of different kinds or with the optical endoscope fitted with the externally fitted camera having a plurality of solid state imaging devices of different kinds, if such an abnormality as the break of the signal transmitting cable of the solid state imaging device which is being used or the deterioration or break of the imaging device occurs, the image will vanish, the observing visual field will be lost and the continuation of the inspection will be likely to be obstructed.

Further, the endoscope is generally used together with a light source apparatus outputting an illuminating light. As disclosed in the publication, for example, of Japanese patent application laid open No. 61588/1986, such light source apparatus is provided with an adjusted light controlling part controlling the light amount of the illuminating light. In this adjusted light controlling part, only the low frequency component of the output signal from the solid state imaging device built-in in the tip part, for example, of an electronic endoscope is extracted and is compared with the reference potential, in case it is larger than the reference voltage, the diaphragm member will be contracted and, in case it is smaller than the reference voltage, the diaphragm member will be opened to control the light amount.

However, in case such trouble as the failure of the solid state imaging device or the break of the signal transmitting cable occurs, the signal from the solid state imaging device will become smaller than the reference voltage and the diaphragm member will remain open.

Therefore, in case such trouble occurs during the diagnosis, a large light amount will be emitted out of the endoscope tip and will likely be burned, for example, the stomach wall of the patient or the light guide. Particularly, in the endoscope by the color mosaic type imaging system, as the light source does not need such RGB rotary filter or the like as in the frame sequential system, the illuminating light emitted from the light source will be radiated directly to the stomach wall or the like without being attenuated by the RGB rotary filter, and the danger will be larger.

SUMMARY OF THE INVENTION

An object of the present invention is to provide an electronic endoscope apparatus wherein, even in case any system of the signals of a plurality of systems output from at least one solid state imaging device becomes abnormal and a part of the signal read out of the solid state imaging device cannot be normally obtained, the observed endoscope image will be prevented from being lost and the safety of the endoscope inspection will be able to be elevated.

Another object of the present invention is to provide an electronic endoscope apparatus wherein, in case a part of the signals read out of the solid state imaging device having a plurality of output ends cannot be normally obtained, the observed endoscope image will be prevented from being lost and the safety of the endoscope inspection will be able to be elevated.

Another object of the present invention is to provide an electronic endoscope apparatus wherein, in case the signal read out of the solid state imaging device in the case of the endoscope inspection is not normally obtained, the burn in the observed position within the body cavity of the patient by the excessive light amount of the illuminating light and the burned loss of the light guide will be able to be prevented.

Another object of the present invention is to provide an electronic endoscope apparatus wherein the safety is improved in the endoscope inspection with the electronic endoscope provided with at least one solid state imaging device.

Further another object of the present invention is to provide an electronic endoscope apparatus wherein the safety is improved in the endoscope inspection with the optical endoscope fitted with the externally fitted camera having at least one solid state imaging device.

Briefly the electronic endoscope apparatus of the present invention comprises an imaging means outputting signals of a plurality of systems from at least one solid state imaging device, a plurality of signal transmitting means transmitting signals of a plurality of systems output by at least one solid state imaging device of the above mentioned imaging means, a signal processing means processing by the corresponding processing modes the respective signals transmitted by the above mentioned plurality of signal transmitting means, a signal monitoring means judging whether the respective signals transmitted by the above mentioned plurality of signal transmitting means are normal or not and a processing mode changing means changing the processing modes of the above mentioned signal processing means on the basis of the judged result of the above mentioned signal monitoring means.

The other features and advantages of the present invention will become apparent enough with the following explanation.

BRIEF DESCRIPTION OF THE DRAWINGS

FIG. 1 is a formation diagram of an electronic endoscope apparatus.

FIG. 2 is a schematic formation diagram of a line transfer type CCD provided with horizontal transfer registers in two steps.

FIG. 3 is an explanatory diagram showing the operation of the line transfer type CCD shown in FIG. 2.

FIGS. 4 to 7 show the first embodiment of the present invention.

FIG. 4 is a schematic general formation diagram of an electronic endoscope apparatus.

FIG. 5 is a circuit formation diagram of an essential part of an electronic endoscope apparatus.

FIG. 6 is an appearance view of an electronic endoscope apparatus.

FIG. 7 is a concrete circuit formation diagram of a signal monitoring circuit.

FIG. 8 is a circuit formation diagram of an essential part of an electronic endoscope apparatus.

FIG. 9 is a circuit formation diagram of a signal monitoring circuit.

FIG. 10 is a circuit formation diagram of an essential part of an electronic endoscope apparatus.

FIG. 11 is a circuit formation diagram of the second signal processing circuit.

FIG. 12 is a formation diagram showing a part of a CCD.

FIG. 13 is an explanatory diagram showing the operation of a CCD.

FIG. 15 is a circuit formation diagram of an essential part of an electronic endoscope apparatus.

FIG. 16 is a circuit formation diagram of the second signal processing circuit.

FIG. 20 is a formation diagram of an electronic endoscope apparatus.

FIG. 21 is an explanatory diagram showing an output signal of an LPF in the normal state.

FIG. 22 is an explanatory diagram showing an output signal of an LPF in the abnormal state.

FIG. 23 is a formation diagram of an electronic endoscope apparatus.

FIG. 24 is an explanatory view of a turret plate.

FIG. 26 is an explanatory diagram relating to a signal monitoring means.

FIG. 27 is a circuit formation diagram of a timer.

FIG. 28 is a timing chart for explaining a timer operation.

FIG. 29 is a circuit formation diagram of a comparator.

FIG. 30 is an explanatory diagram of the operation of a comparator.

FIG. 31 is a circuit formation diagram of a signal monitoring circuit.

DETAILED DESCRIPTION OF THE PREFERRED EMBODIMENTS

Figure 1:
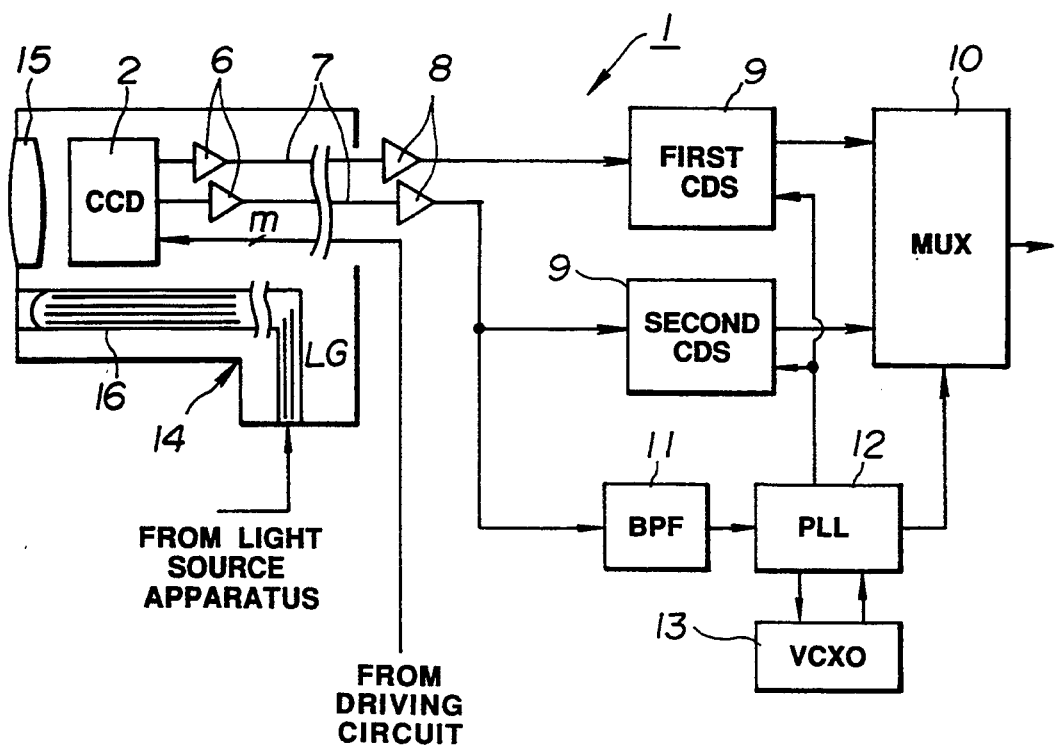
FIGS. 1 to 3 show related art.
Figure 2:
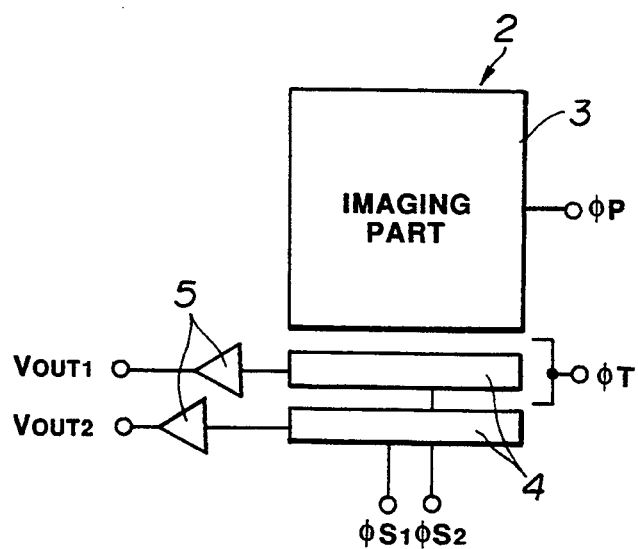
Figure 3:
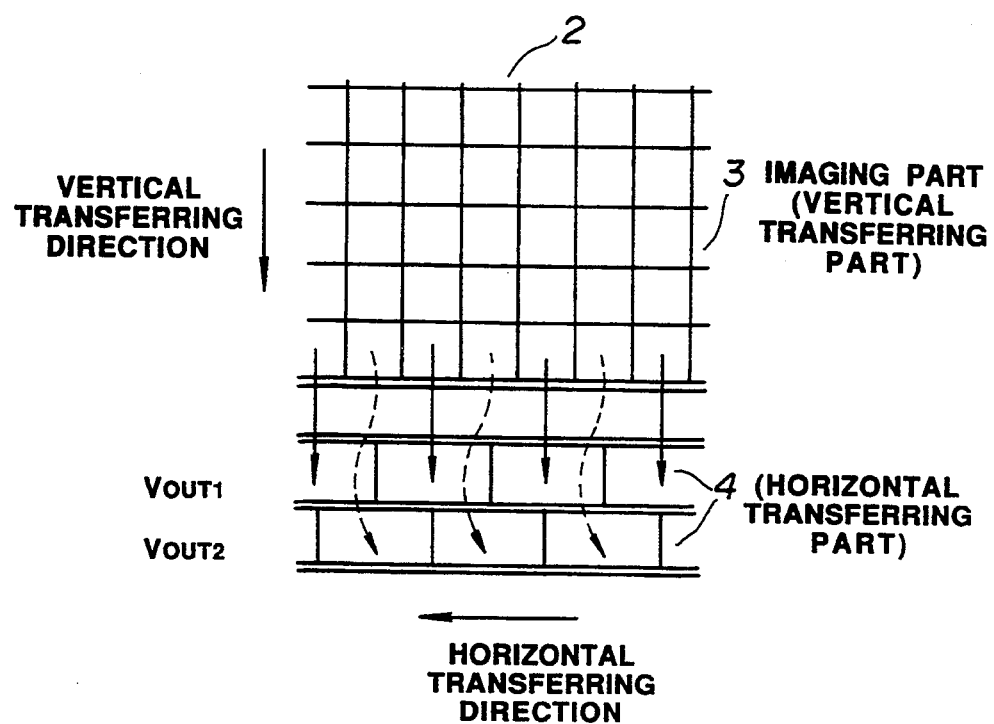

FIGS. 4 to 7 show the first embodiment of the present invention.

An electronic endoscope apparatus 20 shown in FIG. 4 comprises a solid state imaging device 21 provided within such imaging means as an electronic endoscope, not illustrated, or such imaging means as an externally fitted camera fitted to an optical endoscope and outputting n image signals, n buffers 22 and n coaxial cables 23 as signal transmitting means, 1st to nth signal processing circuits 24 as signal processing means, a synthetic circuit 25 also as a signal processing means, a signal monitoring circuit 26 as a signal monitoring means and a signal processing mode controlling circuit 27 as a processing mode changing means.

The n imaging signals output by the above mentioned solid state imaging device 21 are relayed by the n buffers 22, are further transmitted by the n coaxial cables 23, are input into the 1st to nth signal processing circuits 24 and are processed. The respective signals processed by these 1st to nth signal processing circuits 24 are synthesized by the synthesizing circuit 25 and are output to an image signal processing circuit in the later step.

Also, the n image signals output by the above mentioned solid state imaging device 21 are input into the signal monitoring circuit 26 through the above mentioned coaxial cables 23 and it is monitored whether the respective imaging signals are normally output or not. The processing modes of the above mentioned signal processing circuit 24 and synthetic circuit 25 are controlled by the signal processing mode controlling circuit 27 so that the best image may be secured on the basis of the judged result output by this signal monitoring circuit 26. Even if at least one imaging signal of the n imaging signals output by the above mentioned solid state imaging device 21 is not input into the 1st to nth signal processing circuits 24, the processing mode will be switched and a signal not lacking the image will be output to an image signal processing circuit, not illustrated, in the later step.

The solid state imaging device 21 is driven and controlled by m driving signals of a driving circuit, not illustrated.

Figure 6:
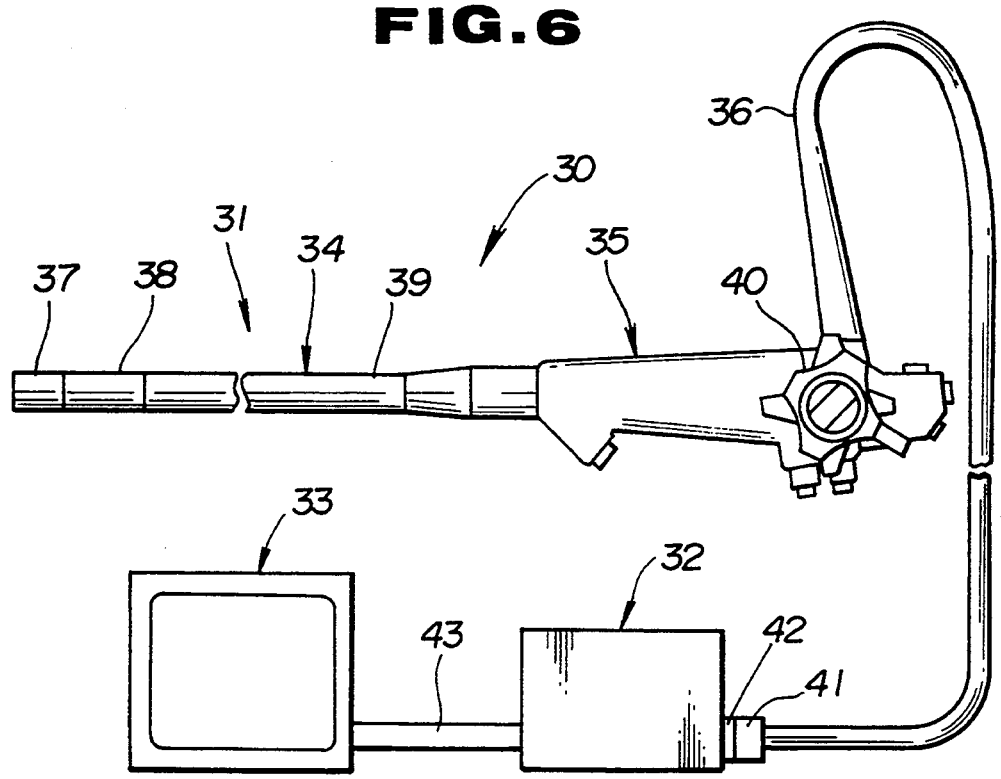

An embodiment of the electronic endoscope apparatus 20 shown in FIG. 4 is shown in FIGS. 5 and 6. As shown in FIG. 6, the electronic endoscope apparatus 30 as an embodiment has an electronic endoscope 31 and an image signal processing apparatus 32 connecting this electronic endoscope 31 to feed an illuminating light and processing the signal from the electronic endoscope 31 to obtain an observed image of the examined object. A monitor 33 displaying the endoscope image is connected to this image signal processing apparatus 32.

The above mentioned electronic endoscope 31 is provided with an elongate insertable part 34, a thick operating part 35 connected to this insertable part 34 on the rear end side and a universal cable 36 extended from the side of this operating part 35.

A rigid tip part 37 is provided on the tip side of the above mentioned insertable part 34 and a bendable part 38 is provided on the rear side adjacent to this tip part 37. Further, a flexible soft part 39 is connected to the rear part of this bendable part 38. The above mentioned bendable part 38 can be bent vertically and horizontally by operating a bending operating knob 40 provided on the above mentioned operating part 35.

A connector 41 is provided at the rear end of the above mentioned universal cable 36 and is connected to a connector receptacle 42 provided on an image signal processing apparatus 32. The above mentioned image signal processing apparatus 32 is connected with a monitor 33 through a signal cable 43.

FIG. 5 shows a circuit formation of the electronic endoscope apparatus 30. A charge coupled device (CCD) 53 as a solid state imaging device has two outputs. The electronic endoscope apparatus 30 comprises, as signal processing means, two correlated double sampling (CDS) circuits 57a and 57b a selector 59 as a signal selecting circuit consisting of an analogue switch, a multiplexer (MUX) circuit 60 as a synthesizing circuit, a band pass filter (BPF) 61 as a carrier extracting circuit, a PLL (Phase Locked Loop) circuit 62 as a sampling clock producing circuit and a voltage controlling crystal oscillator (VCXO) 63 and comprises a signal monitoring circuit as a signal monitoring means and processing mode changing means.

In the above mentioned electronic endoscope 31, a light guide fiber bundle 50 leading the illuminating light from the light source apparatus is inserted through the interior so that the illuminating light may be radiated to the object to be examined through an illuminating optical system 51 arranged in the tip (tip part 37). Also, an objective optical system 52 and a CCD 53 converting the reflected light from the examined object to an electric signal and outputting two signals are provided within the tip (tip part 37) of the above mentioned electronic endoscope 31. This CCD 53 is driven by a plurality of driving signals of a driving circuit, not illustrated, to output signals and has the reading timing controlled.

The respective output signals $V_{out1}$ and $V_{out2}$ of the CCD 53 are output, respectively, to the first and second correlated double sampling (CDS) circuits 57a and 57b (represented by CDS circuits 57 in some cases) through buffers 54, coaxial cables 55 and amplifiers 56 and are output to the signal monitoring circuit 58 and selector 59. The above mentioned CDS circuits 57 correlatively doubly sample the signals by the timing of the later described CDS clock to remove the carrier and output them.

The multiplexer (MUX) circuit 60 synthesizes the two signals output by the above mentioned CDS circuit 57 into one signal by the timing of the later described CDS clock and outputs it to the image signal processing circuit in the later step.

The above mentioned signal monitoring circuit 58 judges whether the two signals read out of the CCD are normally output or not and switches the above mentioned selector 59 on the basis of the normal/abnormal judged result. Also, this signal monitoring circuit 58 controls the signal synthesizing mode of the MUX circuit on the basis of the above mentioned judged result and outputs signals to a display controlling circuit 70a.

By the abnormal signal from the signal monitoring circuit 58, the above mentioned display controlling circuit 70a outputs a display signal to a displaying apparatus 70 as an abnormality notifying means to notify that one or both of the signals $V_{out1}$ and $V_{out2}$ read out of the CCD is or are abnormal. The displaying apparatus 70 as this abnormality notifying means may be, for example, the monitor 33 or may be provided separately from the monitor 33.

The abnormality notifying means may be one issuing an alarm directly by the abnormal signal from the signal monitoring circuit 58 such as, for example, a buzzer.

On the other hand, in response to the instruction of the signal monitoring circuit 58, the above mentioned selector 59 selects one of the two signals read out of the CCD 53 and outputs it to a BPF 61. The BPF 61 extracts only the carrier clock from the signal read out of the CCD, produces a CDS clock synchronized in the phase with the carrier clock of one signal read out of the CCD by the PLL circuit 62 and VCXO 63 and outputs it to the above mentioned CDS circuit 57 and MUX circuit 60.

Figure 7:
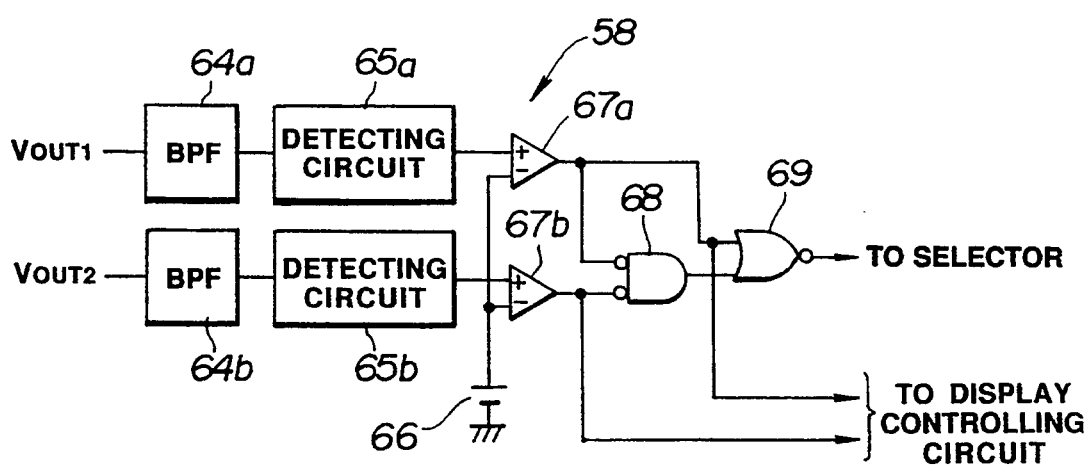

FIG. 7 shows actual formation of the above mentioned signal monitoring circuit 58 which comprises BPF's 64a and 64b inputting respectively the signals $V_{out1}$ and $V_{out2}$ read out of the CCD, detecting circuits 65a and 65b detecting the signals output by the BPF's 64a and 64b, comparators 67a and 67b comparing the respective output signals detected by the detecting circuits 65a and 65b with the same reference power source 66 and outputting the judged signal to the above mentioned MUX circuit 60 and display controlling circuit 70a, an AND gate 68 reversing and inputting the above mentioned judged signals of the comparators 67a and 67b and a NOR gate 69 inputting the judged signal from the comparator 67a into one terminal, inputting the output signal of the above mentioned AND gate into the other terminal and outputting it as a switching signal to the above mentioned selector 59.

In this signal monitoring circuit 58, in case the detected signals $V_{out1}$ and $V_{out2}$ read out of the CCD are smaller than the voltage value of the reference power source 66, that is, in case the signal level is abnormally low or in case the signals are not completely input due to the break or the like of the coaxial cable, the comparators 67a and 67b will be on a low level (L level) and the MUX circuit 60 and display controlling circuit will be notified of the abnormality. In case the signals $V_{out1}$ and $V_{out2}$ read out of the CCD are larger than the voltage value of the reference power source, the comparators 67a and 67b will be on a high level (H level) and the MUX circuit 60 and display controlling circuit 70a will be notified of the normality.

In case both of the signals $V_{out1}$ and $V_{out2}$ read out of the CCD are output and in case only the signal $V_{out1}$ read out of the CCD is normally input, the signal monitoring circuit 58 will output the signal $V_{out1}$ read out of the CCD to the BPF 61 through the selector 59. Further, in case only the signal $V_{out2}$ read out of the CCD is normally input, the signal monitoring circuit 58 will switch the selector 59 to output the signal $V_{out2}$ read out of the CCD to the BPF 61.

The above is arranged as in Table 1.

TABLE 1

| Signals read out of CCD 53 | Output of comparator 67a | Output of comparator 67b | Output of NOR gate 69 | Output of selector 59 |
|---|---|---|---|---|
| Both $V_{OUT1}$ and $V_{OUT2}$ are normal | H | H | L | $V_{OUT1}$ |
| $V_{OUT1}$ is normal, $V_{OUT2}$ is abnormal | H | L | L | $V_{OUT1}$ |
| $V_{OUT1}$ is abnormal, $V_{OUT2}$ is normal | L | H | H | $V_{OUT2}$ |
| Both $V_{OUT1}$ and $V_{OUT2}$ are abnormal | L | L | L | $V_{OUT1}$ |

On the other hand, in the MUX circuit 60, the signal synthesizing mode can be switched in response to the normal/abnormal signal from the signal monitoring circuit 58. That is to say, in the MUX circuit 60, in case one signal read out of the CCD is abnormal, by using only the normal signal read out of the CCD, the lacking (abnormal) signal read out of the CCD will be output through the interpolation with the normal signal read out of the CCD.

In this formation, in case both of the signals $V_{out1}$ and $V_{out2}$ read out of the CCD are normally output, the CDS circuit 57 will make a correlated double sampling by the timing of the CDS clock synchronized in the phase with the carrier clock of the read out signal $V_{out1}$ to remove the carrier and the MUX circuit 60 will synthesize the signals output by the CDS circuit 57 into one signal and will output it.

Also, in case the signal $V_{out2}$ read out of the CCD is abnormal, the first CDS circuit 57a will process the signal with the CDS clock corresponding to the side of the signal $V_{out1}$ read out of the CCD the same as in the above and the MUX circuit 60 will output the normal output signal from the first CDS circuit 57a through switching the signal synthesizing mode by the abnormal signal from the comparator 67b.

Further, in case the signal $V_{out1}$ read out of the CCD is abnormal, the signal monitoring circuit 58 will instruct the selector 59 to be switched and the CDS circuits 57 will feed the CDS clock corresponding to the side of the signal $V_{out2}$ read out of the CCD. The MUX circuit 60 will output the normal output signal from the second CDS circuit 57a through switching the signal synthesizing mode by the abnormal signal from the comparator 67a.

In this embodiment, as the pixel information of the CCD 53 is read out at a high speed within a predetermined time and the CDS circuit 57 makes a sampling by the CDS clock synchronized in the phase with the carrier clock of one signal read out of the CCD, irrespective of the length of the coaxial cables 55, a stable sampling can be attained and, as a result, the 1/f noise can be greatly improved.

Further, in this embodiment, in case one of the signals $V_{out1}$ and $V_{out2}$ read out of the CCD is not normally input due to the failure of the buffers 54, amplifiers 56 and CCD 53 or the break of the coaxial cables 55, the lacking abnormal read out signal will be output through the interpolation with the normal read out signal and therefore the image obtained on the image signal processing circuit side will be able to be prevented from being partly lost like a slit.

Therefore, during the endoscope observation, a part of the image will not suddenly vanish, the observation will not become impossible and a visual field image which can be continuously inspected with the endoscope will be able to be secured. Also, it can be displayed and made known that either (or both) of the signals $V_{out1}$ and $V_{out2}$ read out of the CCD is (or are) abnormal.

Figure 8:
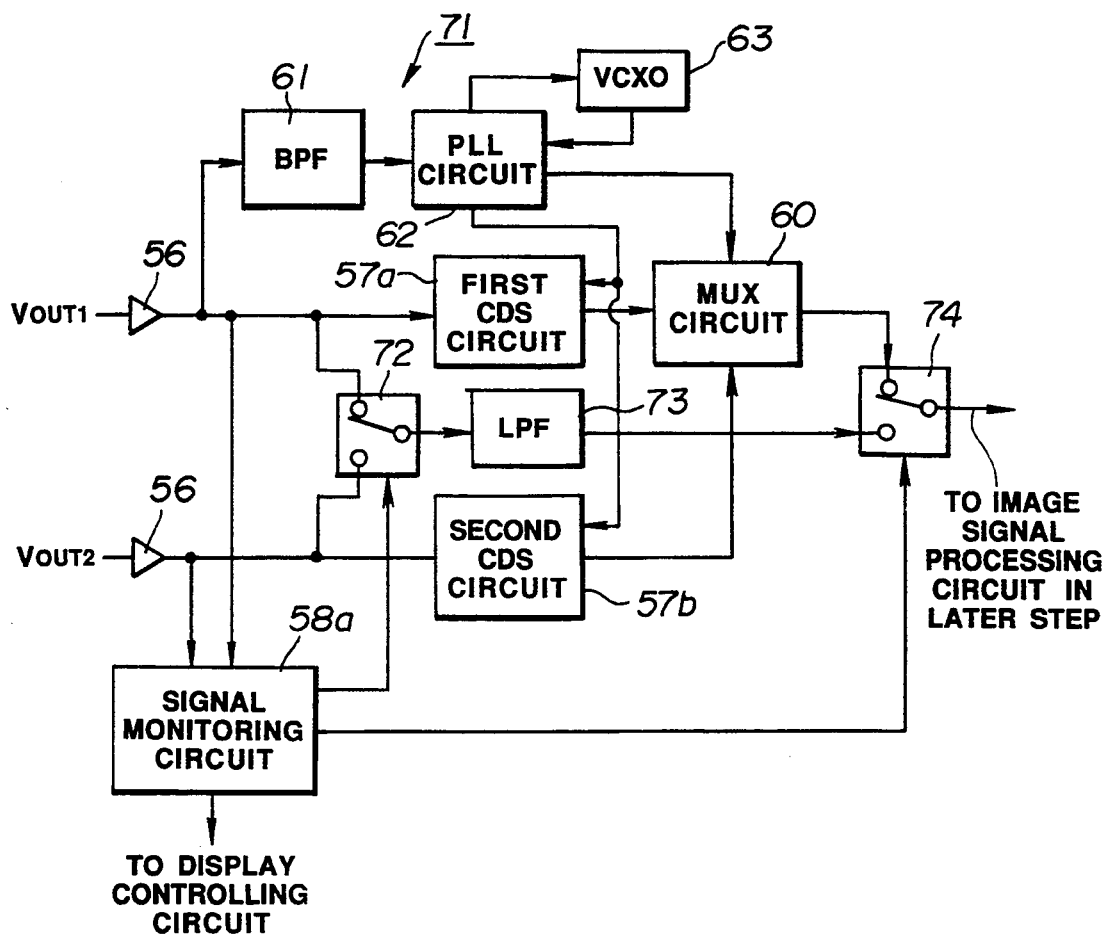
FIGS. 8 and 9 show the second embodiment of the present invention.
Figure 9:
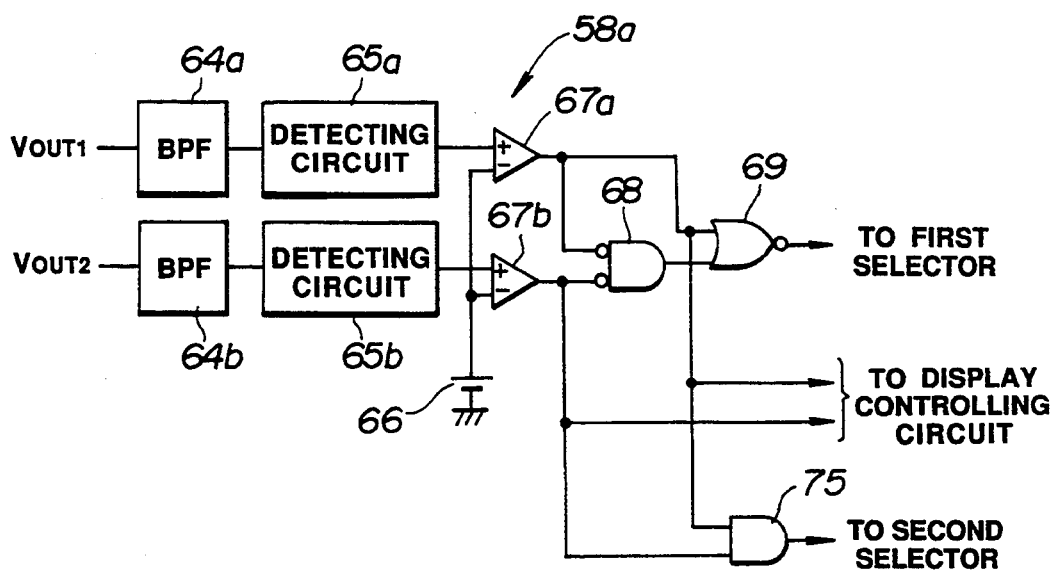

FIGS. 8 and 9 show the second embodiment of the present invention.

In an electronic endoscope apparatus 71 shown in FIG. 8, against the above described first embodiment, in addition to the two CDS circuits 57a and 57b for removing the carrier provided to correspond to the two systems of the signals read out of the CCD, further a first selector 72 as a first signal selecting circuit, an LPF 73 as a carrier removing circuit and a second selector 74 as a second signal selecting circuit are provided in parallel so that, in case one system of the two systems of the signals read out of the CCD becomes abnormal, the normal system will be switched to the above mentioned LPF 73.

In the following respective embodiments, the same formations and operations as in the above described first embodiment shall bear the same reference numerals and shall not be explained.

In the electronic endoscope apparatus 71 of this embodiment, the signal $V_{out1}$ read out of the CCD is input directly into the BPF 61 from one amplifier 56 not through the selector 59 and a CDS clock synchronized in the phase with the carrier clock of the signal $V_{out1}$ read out of the CCD is produced by the PLL circuit 62 and VCXO 63.

On the other hand, the signals $V_{out1}$ and $V_{out2}$ read out of the CCD are input into the first selector 72 through the amplifiers 56 and the CCD read out signal selected and output by the first selector 72 is input into the LPF 73 for removing the carrier component. One of the signals output by this LPF 73 and the signal output by the MUX circuit 60 is selected by the second selector 74 and is output to the image signal processing circuit in the later step not illustrated.

As shown in FIG. 9, the signal monitoring circuit 58a is formed by adding an AND gate 75 to the signal monitoring circuit 58 of the above described first embodiment, the output terminal of the NOR gate 69 is connected to the switching controlling terminal of the first selector 72, the respective output terminals of the comparators 67a and 67b are connected to the input terminal of the AND gate 75 and the output terminal of this AND gate 75 is connected to the switching controlling terminal of the second selector 74.

That is to say, the signal monitoring circuit 58a controls the first selector 72 to select the CCD read out signal which is on the normal level and, in case one of the signals read out of the CCD is abnormal, will control the second selector 74 to select the signal from the LPF 73.

In this embodiment, in case one of the signals $V_{out1}$ and $V_{out2}$ read out of the CCD becomes abnormal due to the break or the like of the coaxial cables 55, the normal read out signal will be selected through the first selector 72, will be fed to the LPF 73 to remove the carrier and then will be sent to the image processing circuit in the later step through the second selector, therefore a part of the image will not suddenly vanish, the observation will not become impossible and the visual field image of which the endoscope inspection can be continued will be able to be secured the same as in the first embodiment.

Further, in this embodiment, when an abnormality occurs, the signal read out of the CCD will be switched to be fed to the LPF 73 and therefore, though the S/N ratio is somewhat lower than in the above described first embodiment, there are advantages that, at the time of switching to the normal system signal read out of the CCD, even in case the signal level of the signal read out of the CCD varies sharply, the signal state will immediately stabilize without waiting until the responding operation of the PLL circuit 62 stabilizes and a stable image will be able to be fed without disturbing the observed image.

FIGS. 10 to 13 show the third embodiment of the present invention.

In this embodiment, the electronic endoscope apparatus is of a simultaneous imaging system using a mosaic filter against the electronic endoscope apparatus of a monochromatic or field sequential imaging system in the first and second embodiments, the circuit formation of the signal processing means of the first embodiment is made a first signal processing circuit and a second signal processing circuit is added to the rear step of this first signal processing circuit.

Figure 10:
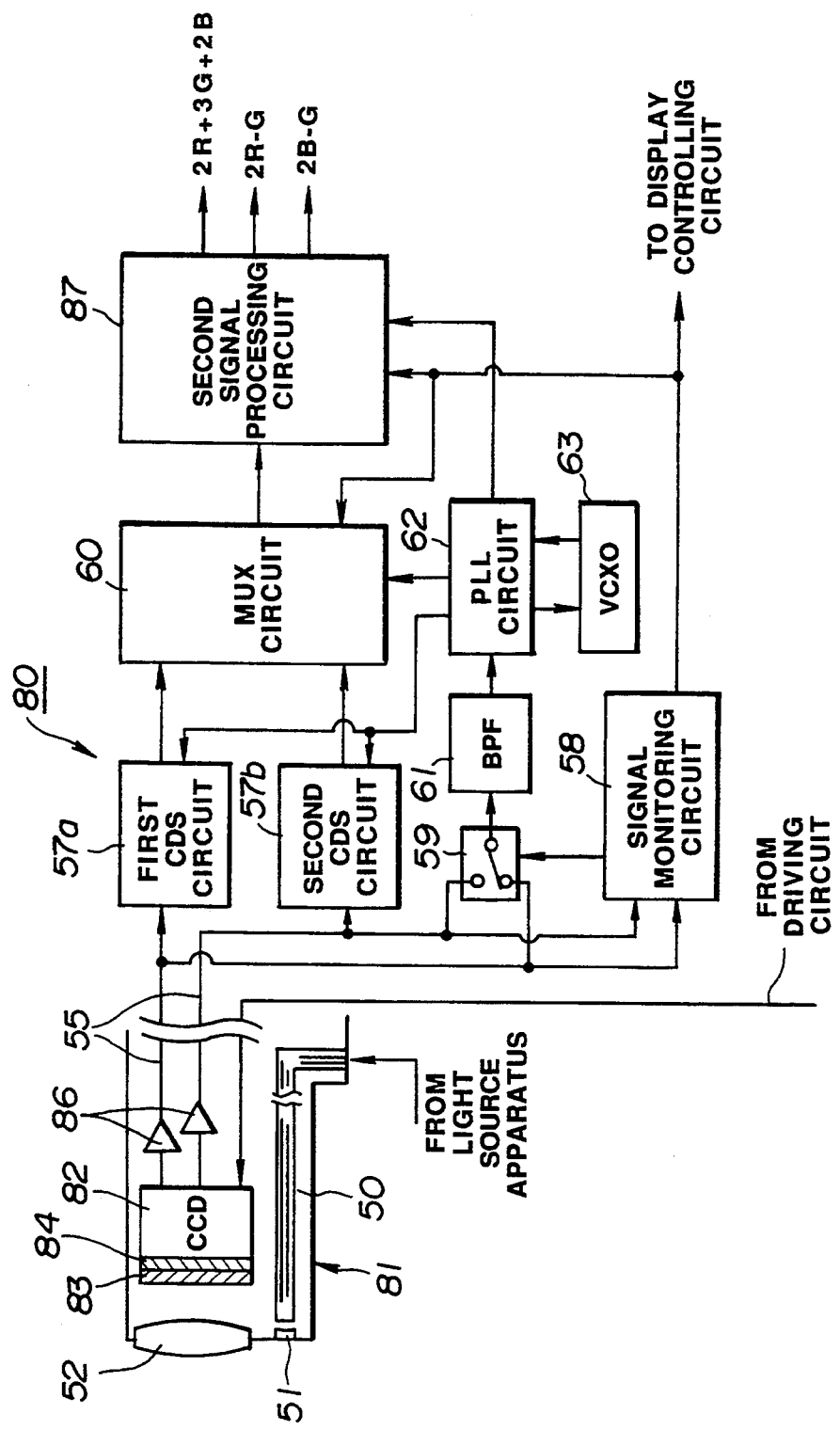
FIGS. 10 to 13 show the third embodiment of the present invention.

As shown in FIG. 10, the electronic endoscope apparatus 80 is an electronic endoscope apparatus of a simultaneous imaging system using a mosaic filter and the electronic endoscope 81 is provided within the tip part with a CCD 82 as a solid state imaging device and on the imaging surface of this CCD with, in the order from the outside, an infrared cutting filter 83 and a mosaic filter 84 in which many respective color filters are mosaic-likely arranged.

Figure 12:
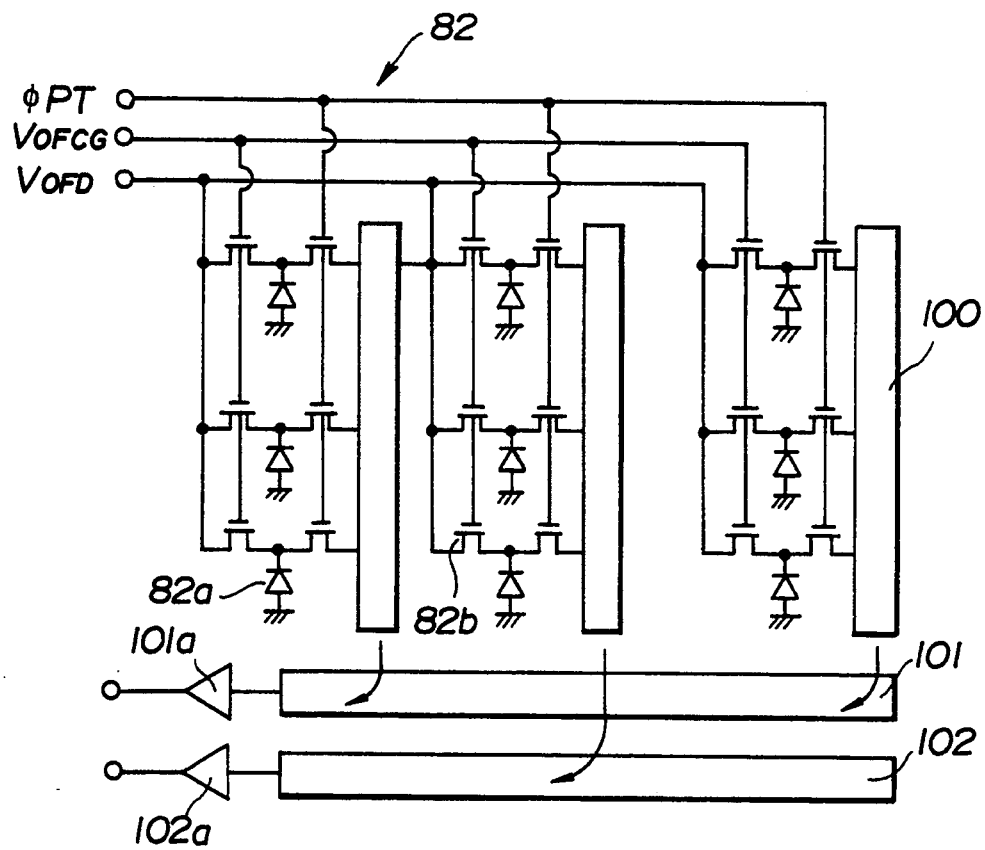
Figure 13:
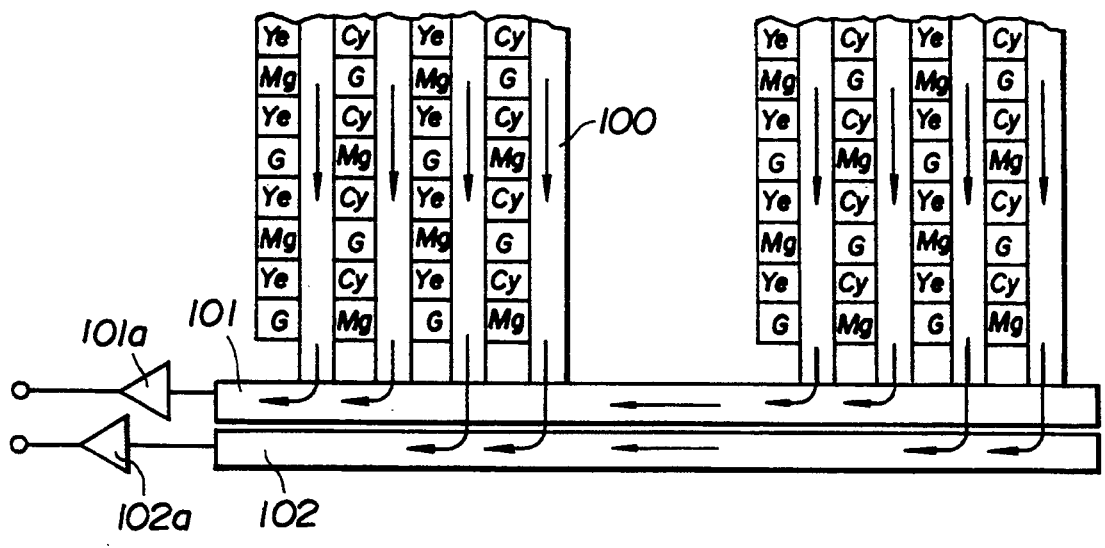

FIGS. 12 and 13 show concrete examples of the CCD 82. This CCD 82 is an interline transfer system CCD provided with two horizontal transfer parts 101 and 102 and is provided on the imaging surface with a mosaic filter 84 having a plurality of colors of cyan (Cy), magenta (Mg), green (G) and yellow (Ye) arranged.

In this CCD 82, as shown in FIG. 13, the pixel information is transferred from vertical transferring parts 100 alternately for two pixels to two horizontal transferring parts in response to the combination of colors of the mosaic filter 84. The reference numeral 82a represents a photodiode, 82b represents a switch device and 101a and 102a represent pre-amplifiers.

As shown in FIG. 10, the electronic endoscope apparatus 80 is provided in the rear step of the MUX circuit 60 with a second signal processing circuit 87 so that in case the two systems of signals read out of the CCD are input, respectively, into the first and second CDS circuits 57a and 57b through the amplifiers 86 and coaxial cables 55 and one of the two systems becomes abnormal, the processing mode of the MUX circuit 60 will be switched from the ordinary signal synthesizing mode synthesizing the respective output signals of the first and second CDS circuits 57a and 57b to a processing mode of interpolating the lacking part of the abnormal system signal through the normal system signal and the processing mode in the second signal processing circuit 87 in the rear step will be controlled to be switched in response to the processing mode of the MUX circuit 60.

Figure 11:
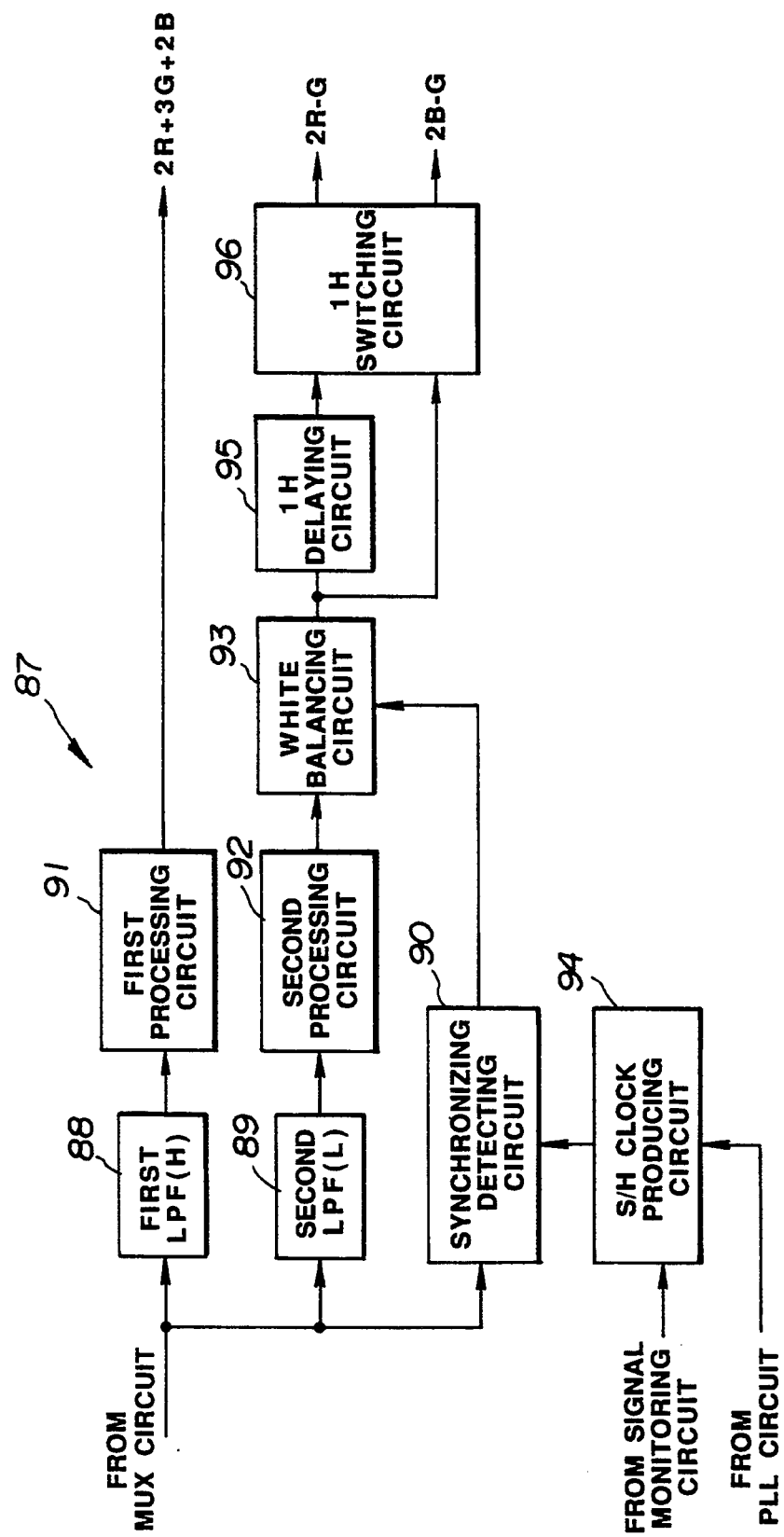

FIG. 11 shows actual example of the second signal processing circuit 87 which comprises a synchronizing detecting circuit 90 synchronizing and detecting the signal output by the MUX circuit 60 to the later described clock to extract a color difference signal and a sampling/holding (S/H) clock producing circuit 94 as a synchronizing detecting clock producing circuit producing a synchronizing detecting clock to be fed to this synchronizing detecting circuit 90.

The signal output by the MUX circuit 60 is passed to a comparatively high band by the first LPF (known as LPF-H hereinafter) 88 and is processed by the first processing circuit 91 to be a "2R+3G+2B" signal and, on the other hand, is passed through the band lower than of the LPF-H by the second LPF (known as LPF-L hereinafter) and is processed by the second processing circuit 92. The output signal of this second processing circuit 92 is input into the white balancing circuit 93.

In the S/H clock producing circuit 94, in case one of the signals read out of the CCD is not input due to the break or the like of the coaxial cable 55, the output signal of the MUX circuit 60 will be an intermittent signal lacking every two pixels and therefore, in response to it, the form of the clock output by the PLL circuit 62 will be changed and a converted clock will be output. In case one of the signals read out of the CCD is abnormal, this clock will be changed by the signal output by the signal monitoring circuit 58.

The above mentioned white balancing circuit 93 corrects the color of the color difference signal extracted as synchronized to the clock from the S/H clock producing circuit 94 by the synchronizing detecting circuit 90. The 1 H delaying circuit 95 is to delay for one horizontal period (1H) the color difference signal having had the color corrected by the white balancing circuit 93.

The 1 H switching circuit 96 produces and outputs a "2R−G" signal and "2B−G" signal from the respective output signals of the 1 H delaying circuit 95 and white balancing circuit 93. The line sequential color difference signal is converted to a simultaneous color difference signal which is output.

In this embodiment, in the electronic endoscope apparatus 80 provided with the simultaneous imaging system electronic endoscope 81 having a CCD provided with a mosaic filter, in case one of the signals $V_{out1}$ and $V_{out2}$ read out of the CCD is not normally input due to the failure of the CCD 82 or amplifiers 86 or the break of the coaxial cables 55, the normal read out signal will be output through the interpolation of the abnormal read out signal, the later step second signal processing circuit 87 side will be also processed by changing the clock of the synchronizing detecting circuit 90 and therefore the endoscope image will be able to be prevented from becoming partial image the endoscope which looks like a slit.

Therefore, during the endoscope observation, a part of the image will not suddenly vanish, the observation will not become impossible and a visual field image in which the endoscope inspection can be continued will be able to be secured. Also, it can be displayed and made known that either (or both) of the signals $V_{out1}$ and $V_{out2}$ read out of the CCD is (or are) abnormal.

Figure 14:
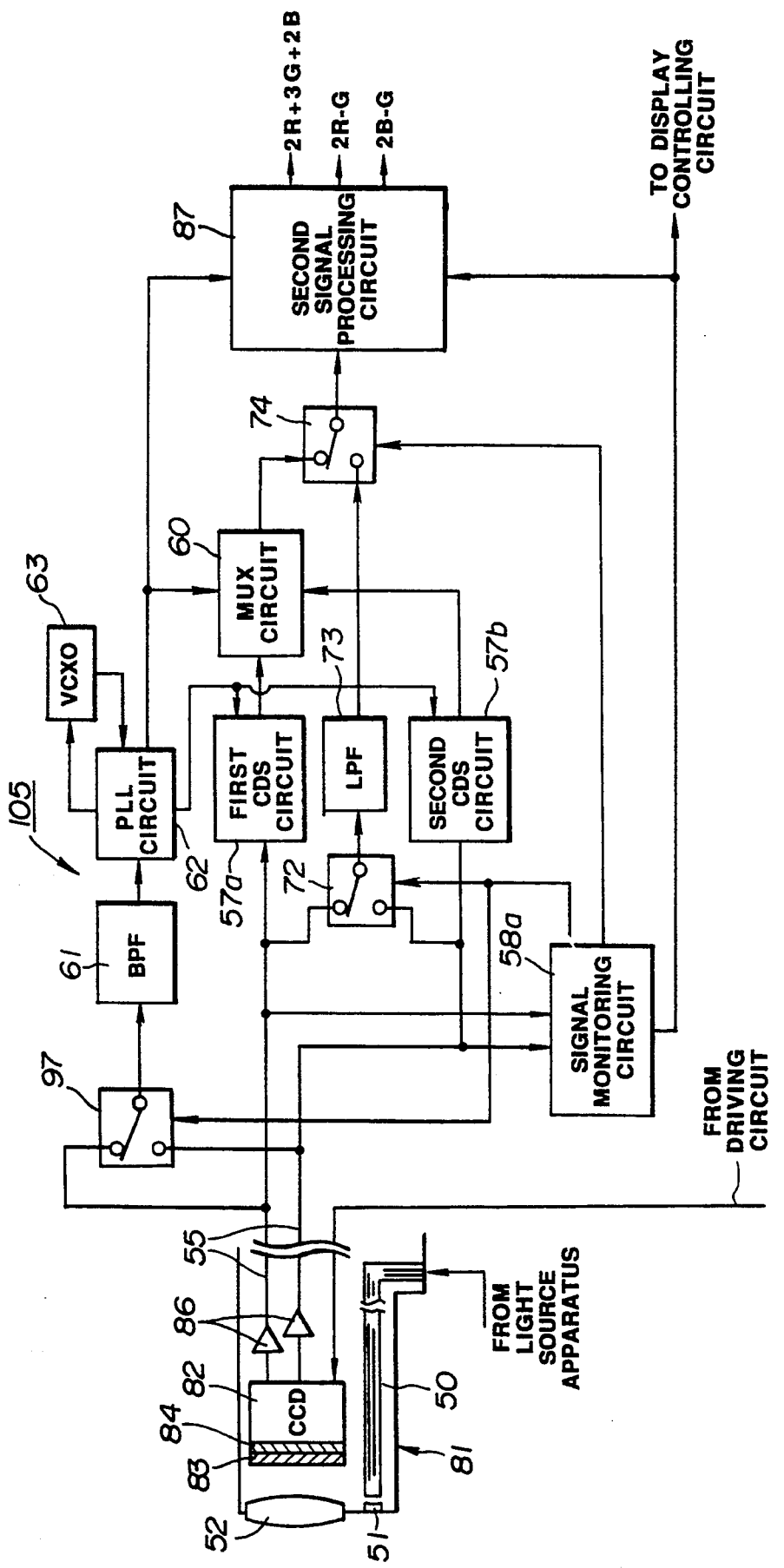
FIG. 14 shows the fourth embodiment of the present invention and is a circuit formation diagram of an essential part of an electronic endoscope apparatus.

FIG. 14 shows the fourth embodiment of the present invention.

The same as the above described third embodiment, this fourth embodiment is an electronic endoscope apparatus of the simultaneous imaging system using a mosaic filter. The third selector 97 which is switched the same as in the first selector 72 by the signal monitoring circuit 58a is added to the circuit formation of the signal processing means of the second embodiment as of the first signal processing circuit to the rear step of which is added the second signal processing circuit 87, the same as in the third embodiment.

In the electronic endoscope apparatus 105 of this embodiment, as shown in FIG. 14, one of the two signals $V_{out1}$ and $V_{out2}$ read out of the CCD 82 is fed to the BPF 61 through the third selector switched by the signal monitoring means 58a and a CDS clock synchronized in the phase to the carrier clock of the signal $V_{out1}$ read out of the CCD is produced by the PLL circuit 62 and VCXO 63.

In case one of the two systems of the signals $V_{out1}$ and $V_{out2}$ becomes abnormal due to the line break or the like, the first selector 72 will be switched by the signal monitoring circuit 58a, the normal system of the signal read out of the CCD will be output to the second signal processing circuit 87 through the LPF 73, the third selector 97 will be switched, the normal system of the signal read out of the CCD will be output to the BPF 61 and the clock fed to the S/H clock producing circuit 94 of the second signal processing circuit 87 from the PLL circuit 62 will be secured.

In this embodiment, the same as in the above described third embodiment, in the electronic endoscope 81 of the simultaneous imaging system having a CCD provided with a mosaic filter, in case one of the signals $V_{out1}$ and $V_{out2}$ read out of the CCD is not normally input due to the failure of the CCD 82 or amplifiers 86 or the break of the coaxial cables 55, the endoscope image will be prevented from becoming a partial image looking like a slit, a visual field image in which the endoscope inspection can be continued will be able to be secured and it will be able to be displayed and made known that which (or both) of the signals $V_{out1}$ and $V_{out2}$ is (or are) abnormal.

Figure 15:
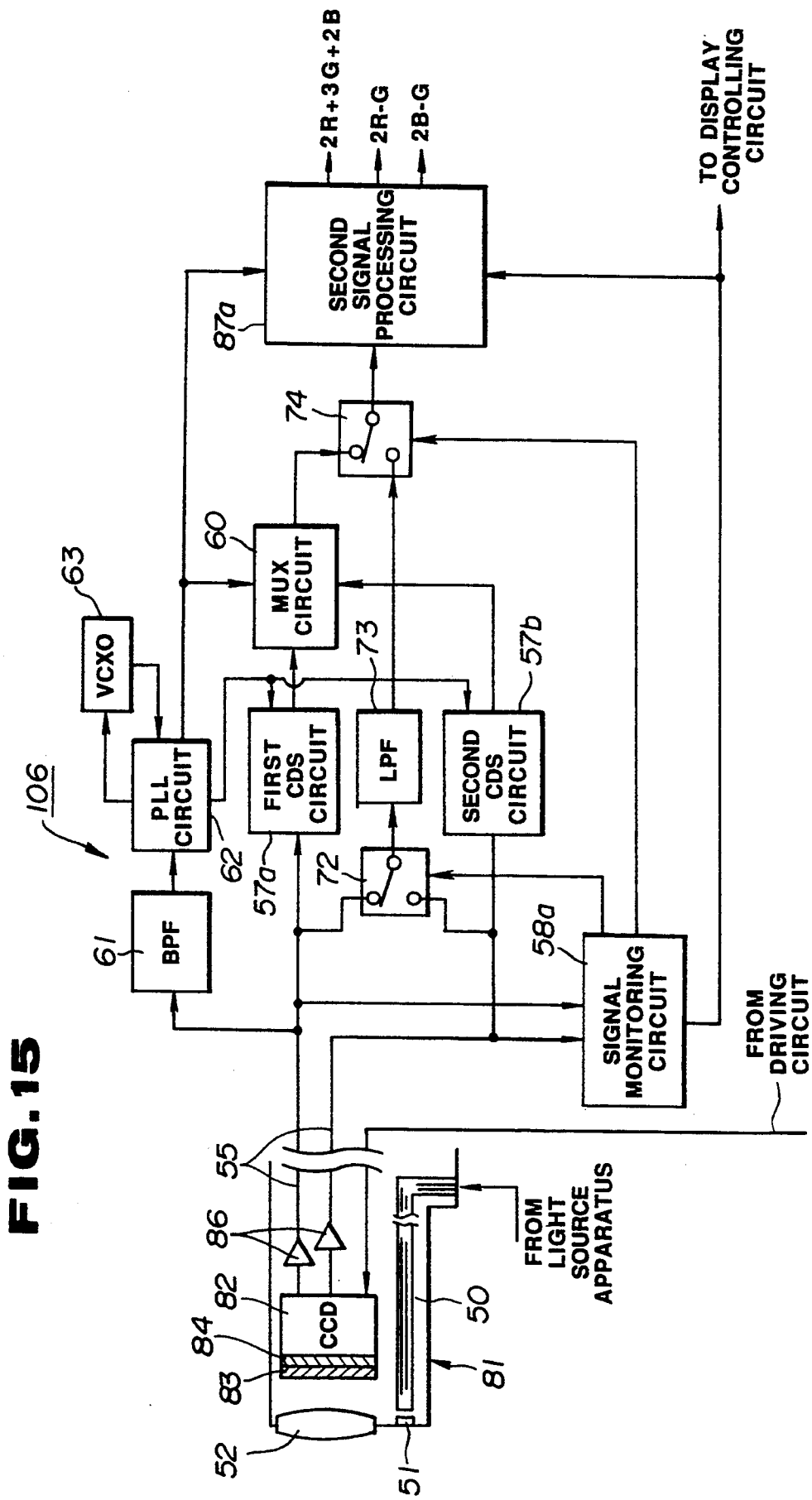
FIGS. 15 and 16 show the fifth embodiment of the present invention.
Figure 16:
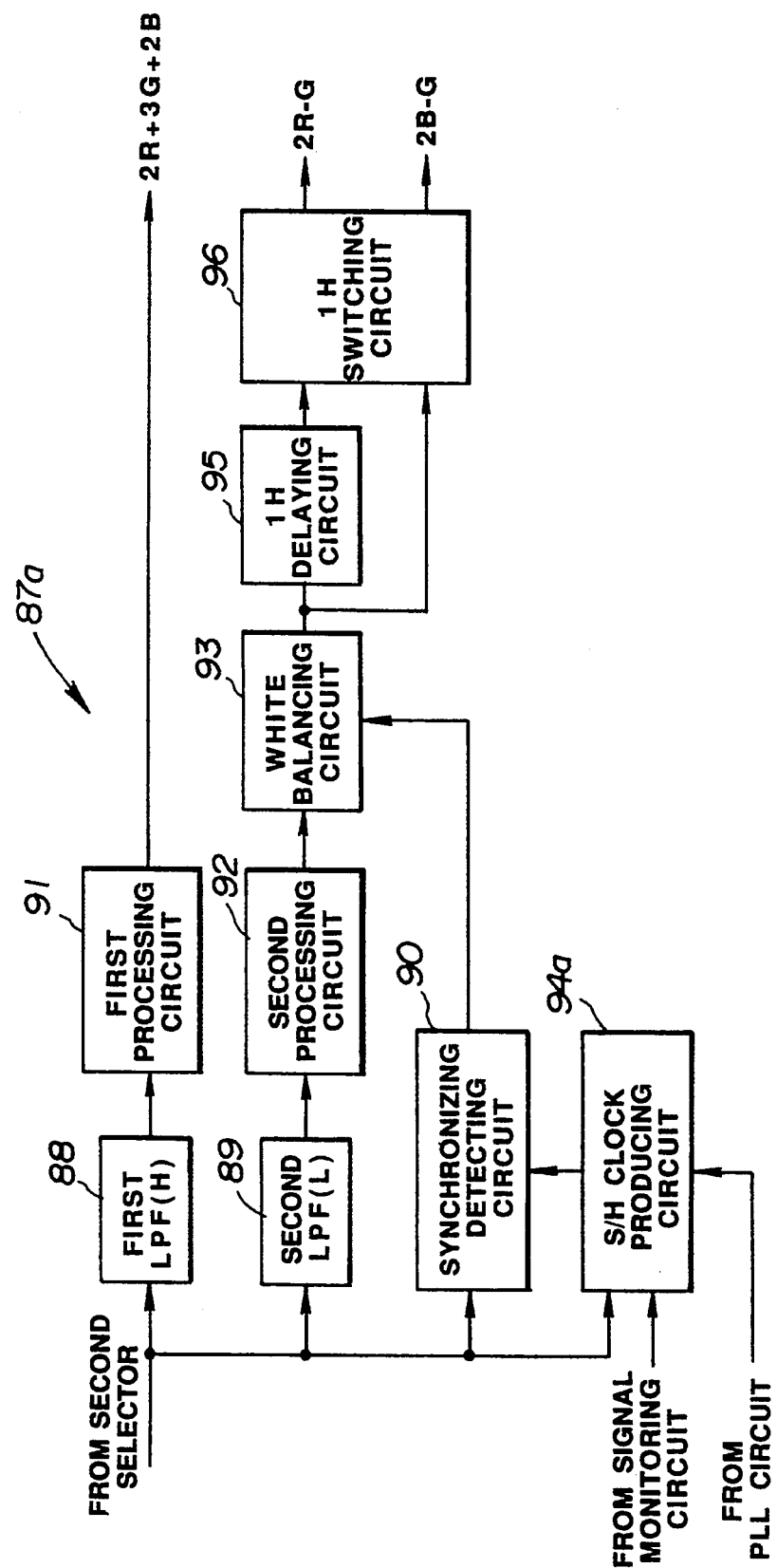

FIGS. 15 and 16 show the fifth embodiment of the present invention.

This embodiment is an electronic endoscope apparatus of the simultaneous imaging system using a mosaic filter the same as in the above described third and fourth embodiments. The circuit formation of the signal processing means of the second embodiment is made a first signal processing circuit and a second signal processing circuit 87a is added to the rear step of this first signal processing circuit.

That is to say, in the electronic endoscope apparatus 106 of this embodiment, as shown in FIG. 15, the third selector is omitted from the circuit formation of the electronic endoscope apparatus 105 of the fourth embodiment (that is to say, the circuit formation of the signal processing means of the second embodiment) and the output terminal of the second selector 74 is connected to the second signal processing circuit 87.

In the second signal processing circuit 87a, as shown in FIG. 16, the formation of the second signal processing circuit 87 in the above described third and fourth embodiments is somewhat modified and the output of the second selector 74 is fed also to the S/H clock producing circuit 94a producing the synchronizing detecting clock in addition to the LPF-H 88, LPF-L 89 and synchronizing detecting circuit 90.

In the S/H clock producing circuit 94a, in case the signal $V_{out1}$ read out of the CCD is not input due the break or the like of the coaxial cable 55, the normal clock will not be fed from the PLL circuit 62 and therefore the synchronizing detecting clock will be produced from the normal signal $V_{out2}$ having passed through the LPF 73.

In such case, the carrier component contained in the signal $V_{out1}$ read out of the CCD will be somewhat weakened by the LPF 73. However, in the above described fourth embodiment, in case the signal $V_{out1}$ read out of the CCD becomes abnormal, it will not be necessary to switch and feed the normal signal $V_{out2}$ to the PLL circuit 62. Therefore, even in case the signal level of the signal $V_{out2}$ read out of the CCD sharply varies, without waiting until the responding operation of the PLL circuit 62 stabilizes, in the second signal processing circuit 87a, the synchronizing detecting clock will be able to be immediately produced.

The other operations and effects are the same as in the fourth embodiment.

Figure 17:
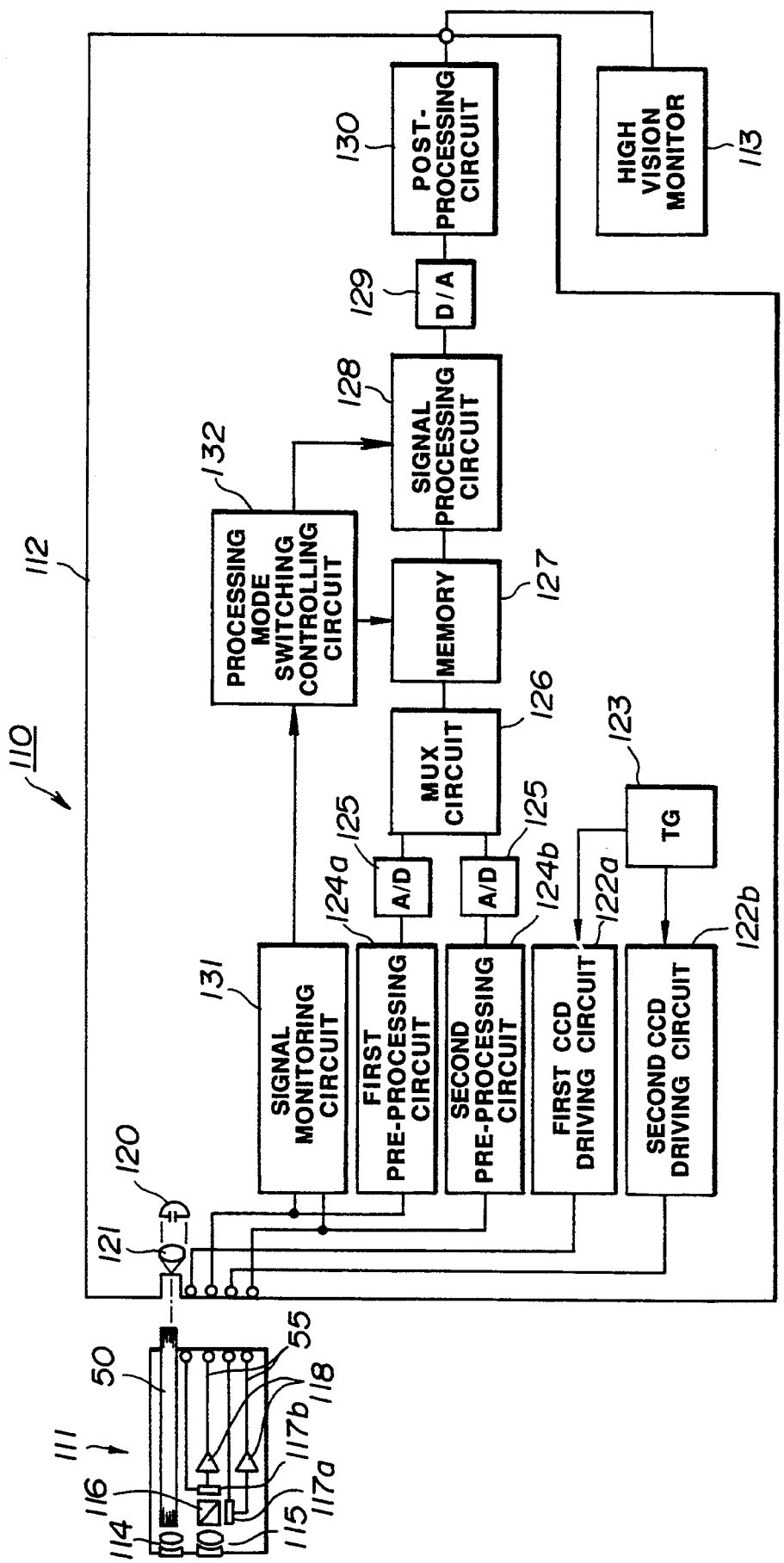
FIG. 17 shows the sixth embodiment of the present invention and is a formation diagram of an electronic endoscope apparatus.

FIG. 17 shows the sixth embodiment of the present invention.

In this embodiment, the present invention is applied to an electronic endoscope apparatus wherein a plurality of CCD's are provided in the tip part of the endoscope and are fitted on the basis of a so-called space pixel displacing method in which the pitches of the respective pixels are arranged as displaced from each other with respect to the optical axis so that a high resolution image may be obtained.

As shown in FIG. 17, the electronic endoscope apparatus 110 of this embodiment has an electronic endoscope 111 and an image signal processing circuit 112 to which this electronic endoscope 111 is connected to obtain an observed image of an examined object and a high vision (high resolution) monitor 113 is connected to display a high resolution image.

The above mentioned electronic endoscope 111 is provided with a flexible insertable part through which is inserted a light guide fiber bundle 50 for radiating to the examined object an illuminating light from a light source apparatus. An illuminating optical system 114 opposed to the emitting end surface of the above mentioned light guide fiber bundle 50 is arranged in the tip part of this insertable part. An objective optical system 115 is arranged also in the tip part of the insertable part of the above mentioned endoscope 111. The first CCD 117a and second CCD 117b are fitted to the two surfaces of a prism 116 arranged in the rear of this objective optical system 115 so that, by the above described space pixel displacing method, the pixel pitches may be displaced by ½ from each other with respect to the optical axis of the objective optical system 115. To the first and second CCD's 117a and 117b are connected, respectively, the buffer amplifiers 118 and coaxial cables 55 as signal transmitting means for transmitting the output signals to the above mentioned image signal processing apparatus 112.

On the other hand, a light source apparatus comprising a light source 120 and light condensing optical system 121 is built-in in the above mentioned image signal processing apparatus 112 so that the illuminating light from the light source 120 condensed by the light condensing optical system 121 may be incident upon the incident end surface of the above mentioned light guide fiber bundle 50.

The above mentioned image signal processing apparatus 112 comprises first and second CCD driving circuits 122a and 122b for driving the first and second CCD's 117a and 117b of the above mentioned electronic endoscope 111, a timing generator (TG) 123 controlling the timing of the driving signals output to the corresponding CCD's from these first and second CCD driving circuits 122a and 122b, a first processing circuit 124a processing the signal read out of the first CCD 117a, a second processing circuit 124b processing the signal read out of the second CCD 117b, an MUX circuit 126 synthesizing the signals from these first and second processing circuits 124a and 124b through A/D converters 125 and storing the synthesized signals in a memory 127, a signal processing circuit 128 as a signal processing means processing the image signals stored in the memory 127 and a post-processing circuit 130 variously correcting the image signals from the signal processing circuit 128 converted to analogue signals through a D/A converter 129 and outputting them to a high vision monitor 113 and further comprises a signal monitoring circuit 131 as a signal monitoring means monitoring whether the signals read out of the two CCD's of the first and second CCD's 117a and 117b are normally output or not and a processing mode switching controlling circuit 132 as a processing mode changing means changing the reading light of the memory 127 and the processing mode of the signal processing circuit 128 by the signal from this signal monitoring circuit 131.

In the above formation, under the control of the TG 123, the first and second CCD driving circuits 122a and 122b generate respectively corresponding CCD driving signals and drive the first and second CCD's 117a and 117b. The optical images of the object imaged by the objective optical system 115 are formed on the imaging surfaces of the first and second CCD's 117a and 117b, are photoelectrically converted and then input into the first and second pre-processing circuits 124a and 124b provided within the image signal processing apparatus 112.

In the above mentioned first and second pre-processing circuits 124a and 124b are made such general signal processes for the signals read out of the CCD's as, for example, the CDS sampling, OB (Optical Black) clamping, color separation, AGC, white balancing and γ correction. The two systems (each system is formed, for example, of luminance and color difference signals) of signals generally processed by the first and second pre-processing circuits 124a and 124b are converted to digital signals by the A/D converters 125, are compensatively synthesized by the MUX circuit 126 and are stored in the memory 127.

The digital image signal read out of the above mentioned memory 127 is displaced in the sampling distance in each scanning line, is therefore interpolated between the adjacent pixels by the signal processing circuit 128 to be a smooth image, is then converted to an analog signal by the D/A converter 129 and is input into the post-processing circuit 130. In the post-processing circuit 130, the image signal is subjected to such various corrections as the band correction and signal level correction and is output to the high vision monitor 113. Thus, by using the two CCD's of the first and second CCD's 117a and 117b, a high resolution endoscope image can be imaged and displayed.

The signals read out of the first and second CCD's 117a and 117b are input also into the signal monitoring circuit 131 so that, in case the CCD breaks or the cable transmitting the CCD driving signal and the signal read out of the CCD breaks, the signal monitoring circuit 131 will sense the abnormality and will output the abnormality sensing signal to the processing mode switching controlling circuit 132 to control the reading light of the memory 127 and the processing mode of the signal processing circuit 128.

As a result, the processing mode of the signal processing circuit 128 is changed from the high resolution processing mode by the space pixel displacing method of the first and second CCD's 117a and 117b to a low resolution image processing mode using only the normal system of the signal read out of the CCD and the image is processed, for example, by the scanning line interpolation so as to be able to be displayed in the high vision monitor 113.

Therefore, even if any failure occurs during the endoscope observation and either of the systems of the first and second CCD's 117a and 117b becomes inactive, the observed visual field in which the inspection can be continued will be able to be secured.

Figure 18:
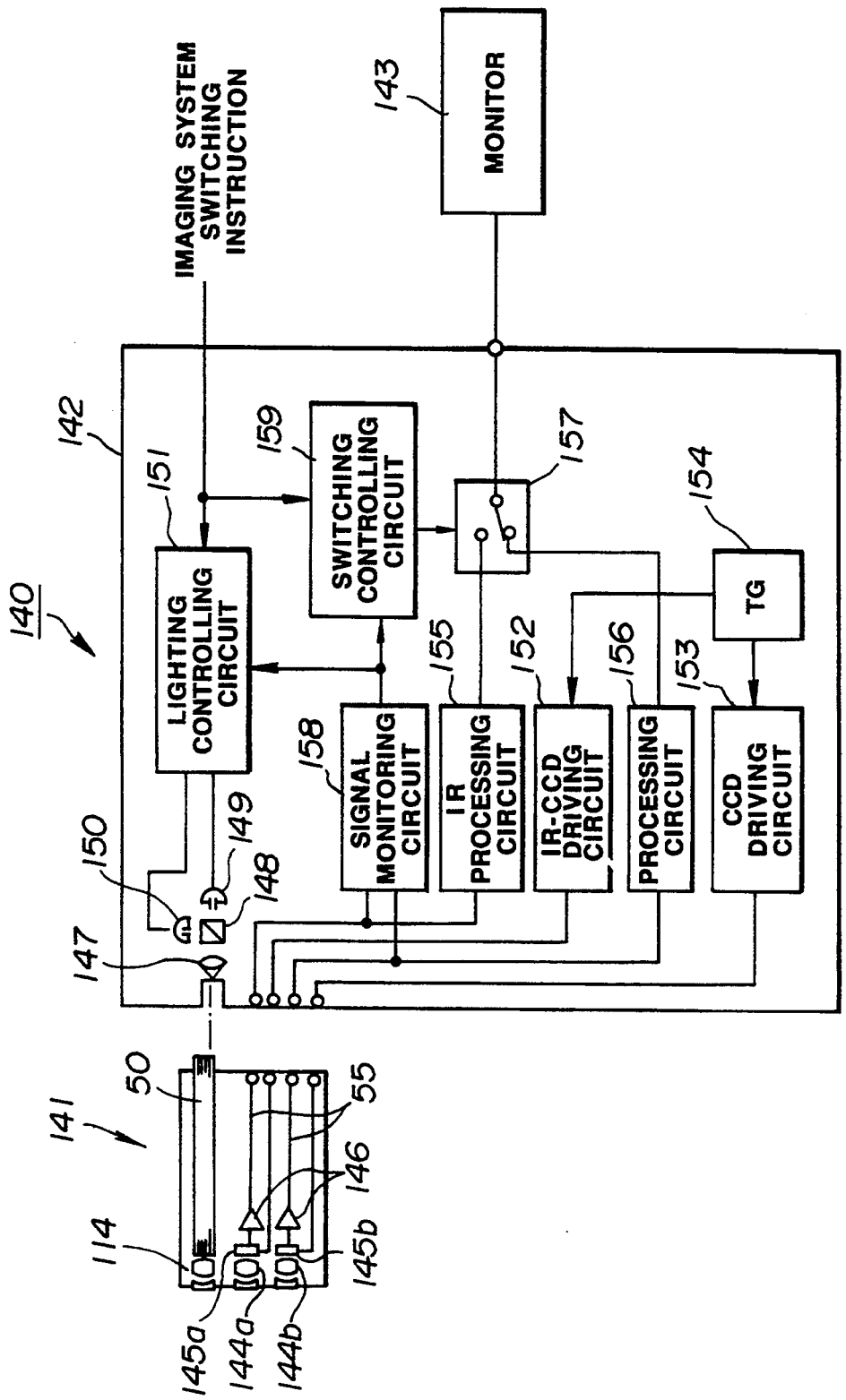
FIG. 18 shows the seventh embodiment of the present invention and is a formation diagram of an electronic endoscope apparatus.

FIG. 18 shows the seventh embodiment of the present invention.

In this embodiment, the present invention is applied to an electronic endoscope apparatus provided in the tip part with an ordinary observing color CCD having, for example, a mosaic-like color filter array pasted on the entire surface and an infrared ray (IR) observing monochromatic CCD so that the ordinary observation and IR observation may be selectively switched over to each other.

As shown in FIG. 18, the electronic endoscope apparatus 140 of this embodiment has an electronic endoscope 141, an image signal processing apparatus 142 for connecting this electronic endoscope 141 to obtain an observed image of an examined object and a monitor 143 connected to this image signal processing apparatus 142 to display the observed image.

The electronic endoscope 141 is provided with a flexible insertable part through which a light guide fiber bundle 50 is inserted. In the tip part of this insertable part, an illuminating optical system 114 opposed to the emitting end surface of the above mentioned light guide fiber bundle 50 is arranged and two imaging systems of an IR imaging system and ordinary imaging system are provided.

That is to say, in the tip part of the above mentioned insertable part, two objective optical systems 144a and 144b are arranged, an IR observing monochromatic CCD 145a is fitted in the image forming position of one objective optical system 144a, a buffer amplifier 146 and coaxial cable 55 as a signal transmitting means for transmitting the output signal to the image signal processing apparatus 142 are connected to this monochromatic CCD 145a to form an IR imaging system. An ordinary observing color CCD 145b is fitted in the image forming position of the other objective optical system 144b and the buffer amplifier 146 and coaxial cable 55 as a signal transmitting means for transmitting the output signal to the image signal processing apparatus 142 are connected to this color CCD 145b to form an ordinary imaging system.

On the other hand, the above mentioned image signal processing apparatus 142 is provided with a white light source 149 to be used for the ordinary observation and an IR observing light source 150 to be used for the IR observation through a light condensing optical system 147 and prism 148 arranged on the incident end surface of the above mentioned light guide fiber bundle 50. These two light sources 149 and 150 are selectively controlled to light by a lighting controlling circuit 151 in response to the observing mode selected by an imaging system switching instructing signal from an operating part not illustrated or a signal from the later described signal monitoring circuit 158.

The above mentioned image signal processing apparatus 142 is provided with an IR-CCD driving circuit 152 driving the monochromatic CCD 145a, a CCD driving circuit 153 driving the color CCD 145b, a TG 154 controlling the timing of the driving signal output to the corresponding CCD from these respective driving circuits 152 and 153, an IR processing circuit as a signal processing means processing the signal read out of the monochromatic CCD 145a, a processing circuit 156 as a signal processing means processing the signal read out of the color CCD 145b and a selector 157 switching the output signal from the IR processing circuit 155 and the output signal from the processing circuit 156 over to each other and outputting them to a monitor 143.

Further, the above mentioned image signal processing apparatus 142 comprises a signal monitoring circuit 158 as a signal monitoring means monitoring whether the signals read out of the two CCD's of the monochromatic CCD 145a and color CCD 145b are normally output or not and a switching controlling circuit 159 controlling switching the above mentioned selector 157 to the IR processing circuit 155 side and the processing circuit 156 side in response to the observing mode selected by the signal from this signal monitoring circuit or the imaging system switching instructing signal so that a signal processing switching means may be formed of this switching controlling circuit 159 and the above mentioned selector 157.

By the above formation, under the control of the TG 154, the IR-CCD driving circuit 152 and CCD driving circuit 153 generate respectively corresponding CCD driving signals and drive respectively the monochromatic CCD 145a and color CCD 145b through the cables within the electronic endoscope 141.

When the imaging system switching instructing signal is input into the lighting controlling circuit 151 and switching controlling circuit 159 from an operating part not illustrated, for example, at the time of the IR observation, the IR observing light source 150 will be selected by the lighting controlling circuit 151 and the IR observed image of the object will be imaged by the IR imaging system and, at the time of the ordinary observation, the white light source 149 will be selected by the lighting controlling circuit 151 and a favorable color image will be imaged by the ordinary imaging system. (In case the color CCD 145b is, for example, of a mosaic filter of Mg, Ye, Cy and G, only the pixels of Mg and Ye will have a sensitivity to infrared rays and therefore, with the IR observing light source 150, the entire picture will become red and will be hard to observe.) By the way, when the white light source 149 is selected for the IR imaging system, a mere monochromatic observed image will be able to be imaged.

The signals imaged by the two imaging systems are input respectively into the corresponding IR processing circuit 155 and processing circuit 156, are processed as predetermined and are input into both input terminals of the selector 157 and, in response to the observing mode selected by the imaging system switching instructing signal, the IR observing image and ordinary observing image are properly switched and are output to the monitor 143.

In such case, it will be monitored by the signal monitoring circuit 158 whether the signals read out of the CCD from the two imaging systems are normally output or not. For example, in case the IR imaging system becomes abnormal during the IR observation, a switching signal will be output to the lighting controlling circuit 151 from the signal monitoring circuit 158, the light source will be switched over to the white light source 149, simultaneously the selector 157 will be switched over to the processing circuit 156 side through the switching controlling circuit 159 and the output to the monitor 143 will be switched over to the ordinary observed image.

On the contrary, in case the ordinary imaging system becomes abnormal, as the monochromatic CCD 145a of the IR imaging system has a sensitivity to the entire wavelength range, the light source will be made the white light source 149, the selector 157 will be switched over to the IR processing circuit 155 side through the switching controlling circuit 159 and the output to the monitor 143 will be switched over to the infrared image system so that a favorable visual field, though monochromatic, will be able to be secured. By the way, in this case, in response to the IR imaging system, the light may be radiated from both of the white light source 149 and IR observing light source 150.

As in the above, in this embodiment, in the electronic endoscope apparatus 140 wherein the ordinary observation and IR observation can be switched over to each other by a simple operation during the endoscope inspection, by the signal monitoring circuit 158 monitoring the abnormality of the signals read out of the CCD's of the two systems of the ordinary imaging system and IR imaging system, in the case of such accident as the break of one CCD or the break of the cable transmitting the driving signal or the signal read out of the CCD, the abnormality will be detected, the light source will be switched over to the light source conforming to the normal imaging system, at the same time, the output to the monitor will be switched and therefore, even when an abnormality occurs, the visual field in which the inspection can be continued will be able to be secured and the safety will be able to be elevated.

Figure 19:
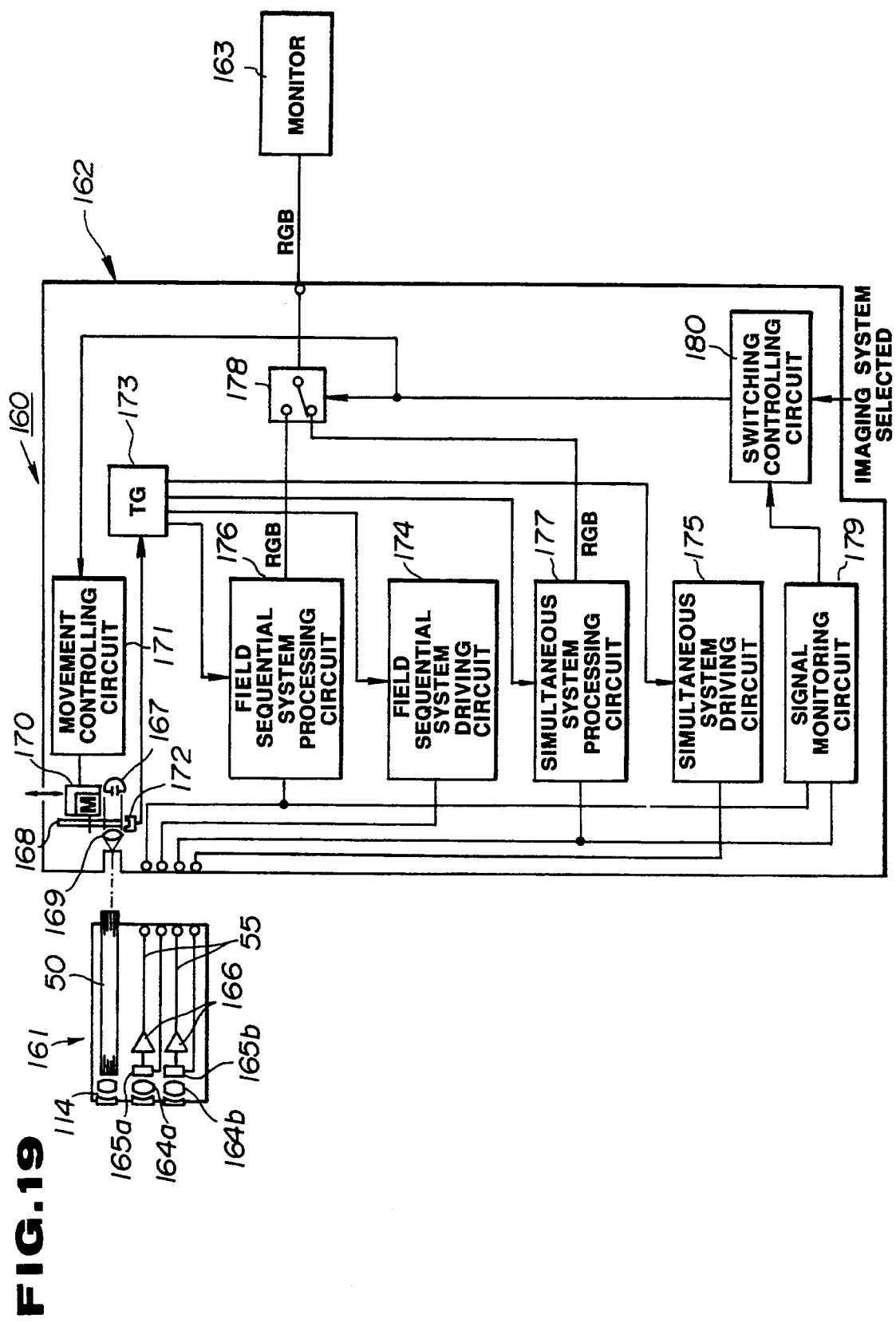
FIG. 19 shows the eighth embodiment of the present invention and is a formation diagram of an electronic endoscope apparatus.

FIG. 19 shows the eighth embodiment of the present invention.

In this embodiment, the present invention is applied to an electronic endoscope apparatus wherein the endoscope is provided in the tip part with a color CCD for the ordinary observation and a monochromatic CCD for the special light observation and further with an illuminating light source and a field sequential filter for the special observation which is insertable into the light path of this light source so that the ordinary observation and special light observation may be freely switched over to each other to make the observation possible.

As shown in FIG. 19, the electronic endoscope apparatus 160 of this embodiment has an electronic endoscope 161, an image signal processing apparatus 162 connecting this electronic endoscope 161 to obtain an observed image of an examined object and a monitor 163 for displaying the observed image connected to this image signal processing apparatus 162.

The above mentioned electronic endoscope 161 is provided with a flexible insertable part through which a light guide fiber bundle 50 is inserted. This insertable part is provided in the tip part with an illuminating optical system 114 opposed to the emitting end surface of the above mentioned light guide fiber bundle 50 and with two objective optical systems 164a and 164b fitted in the image forming positions, respectively, with a monochromatic CCD 165a and color CCD 165b. To the respective CCD's 165a and 165b are connected buffer amplifiers 166 and coaxial cables 55 as a signal transmitting means for transmitting the output signals to the image signal processing apparatus 162.

On the other hand, a white light source 167 is built-in in the above mentioned image signal processing apparatus 162. Further, a filter having a predetermined permeating characteristic is arranged along the periphery of this white light source and a light condensing optical system 169 is arranged as opposed to the incident end of the above mentioned light guide fiber bundle 50 through a rotary filter disc 168 insertable in the light source light path.

The above mentioned rotary filter disc 168 is pivoted to a driving motor 170 and a movement controlling circuit 171 controlling the drive of this driving motor 170 controls the movement to insert the above mentioned rotary filter disc 168 into the light source light path, control its rotation and retreat it out of the light source light path by the signal from the later described switching controlling circuit 180. A sensor 172 is arranged in the peripheral part of the above mentioned rotary filter disc 168 so that the illumination switching timing by the above mentioned rotary filter disc 168 as detected by this sensor 172 may be input into the TG 173.

Also, the above mentioned image signal processing apparatus comprises a field sequential system driving circuit 174, a simultaneous system driving circuit 175, a field sequential system processing circuit 176 as a signal processing means processing the signal read out of the monochromatic CCD 165a, a simultaneous system processing circuit as a signal processing means processing the signal read out of the color CCD 165b and a selector 178 switching the output signal from the field sequential system processing circuit 176 and the output signal from the simultaneous system processing circuit 177 over to each other and outputting them to the monitor 163.

Further, the above mentioned image signal processing apparatus 162 is provided with a signal monitoring circuit 179 as a signal monitoring means monitoring whether the signals read out of the two CCD's of the monochromatic CCD 165a and color CCD 165b are normally output or not and with a switching controlling circuit 180 controlling switching the above mentioned selector 178 to the field sequential system processing circuit 176 side and the simultaneous system processing circuit 177 side by an observing mode corresponding to the signal from this signal monitoring circuit 179 or to the imaging system selecting instructing signal from the operating part not illustrated. A signal processing switching means is formed of this switching controlling circuit 180 and the above mentioned selector 178.

In the electronic endoscope apparatus of this embodiment, for example, when the special light observing mode imaging system selecting instructing signal is input into the switching controlling circuit 180, the selector 178 will be switched over to the field sequential system processing circuit 176 side and the rotary filter disc 168 will be inserted into the light source light path by the movement controlling circuit 171 and will be rotated and controlled so that the spectral characteristic of the sequential illuminating light will be switched in each imaging field. Then, on the basis of the timing signal from the sensor 172, under the control of the TG 173 synchronized with the rotation of the rotary filter disc 168, a CCD driving signal will be generated in the field sequential system driving circuit 174 and the monochromatic CCD 165a at the tip of the electronic endoscope 161 will be driven.

The imaged field sequential image is read out of the monochromatic CCD 165a in each field, is made simultaneous in the field sequential system processing circuit 176, is processed to be a signal as predetermined and is output to the monitor 163 through the selector 178. In such case, for example, three different spectral images will be allotted respectively to R, G and B, will be pseudo-colored and will be displayed in the monitor 163.

On the other hand, when an ordinary observing mode imaging system selecting instructing signal is input into the switching controlling circuit 180 from the operating part not illustrated, the selector 178 will be switched to the simultaneous system processing circuit 177 side, the rotary filter disc 168 will be retreated out of the light source light path by the movement controlling circuit 171 and a continuous white illuminating light by the white light source 167 will be radiated to the object through the light guide fiber bundle 50.

Under the control of the TG 173, a CCD driving signal is generated in the simultaneous system driving circuit 175 and the color CCD 165b at the tip of the electronic endoscope 161 is driven. The ordinary observed image imaged and read out by the color CCD 165b is input into the simultaneous system processing circuit 177, is processed to be a signal as predetermined and is output to the monitor 163 through the selector 178.

In such case, it will be monitored by the signal monitoring circuit 179 whether the signals read out of the two systems of CCD's of the monochromatic CCD 165a and color CCD 165b are normally output or not. In case such accident as the break of the CCD or the break of the cable transmitting the driving signal or read out signal occurs or, for example, in case the system on the monochromatic CCD 165a side becomes abnormal at the time of the special light observation, a switching signal will be output to the switching controlling circuit 180 from the signal monitoring circuit 179, the selector 178 will be switched to the simultaneous system processing circuit 177 side corresponding to the color CCD 165b, the rotary filter disc 168 will be retreated out of the light source light path by the movement controlling circuit 171 and the observing mode will be immediately switched over to the ordinary observing mode by the color CCD 165b.

In case the color CCD 165b side system becomes abnormal at the ordinary observing time, a switching signal will be output to the switching controlling circuit 180 from the signal monitoring circuit 179, the selector 178 will be switched over to the field sequential system processing circuit 176 side corresponding to the monochromatic CCD 165a, the rotary filter disc 168 will be inserted into the light source light path by the movement controlling circuit 171 and the observing mode will be switched over to the special light observing mode by the monochromatic CCD 165b.

That is to say, in case such accident as the break of one CCD or the break of the cable transmitting the driving signal or read out signal occurs, by the signal monitoring circuit 179, the insertion and removal of the rotary filter disc 168 will be controlled in conformity with the normal imaging system and, at the same time, the signal output to the monitor 163 will be switched so that, even when an abnormality occurs, the observing visual field in which the inspection can be continued will be able to be secured.

It is feared that, when the simultaneous system is switched over to the field sequential system, due to the synchronization of the TG 173 with the rotary filter disc 168, the image will be disturbed for a moment. However, In case the image is disturbed, by keeping the rotary filter disc 168 always rotating irrespective of its insertion and retreat into and out of the light source light path, the TG 173 may be always synchronized with the rotary filter disc 168. Even if the present invention is applied to an electronic endoscope apparatus wherein the filters used for the rotary filter disc 168 are made respective filters of R, G and B and the RGB field sequential system and the simultaneous system are made to coexist, the same effect will be obtained.

Figure 20:
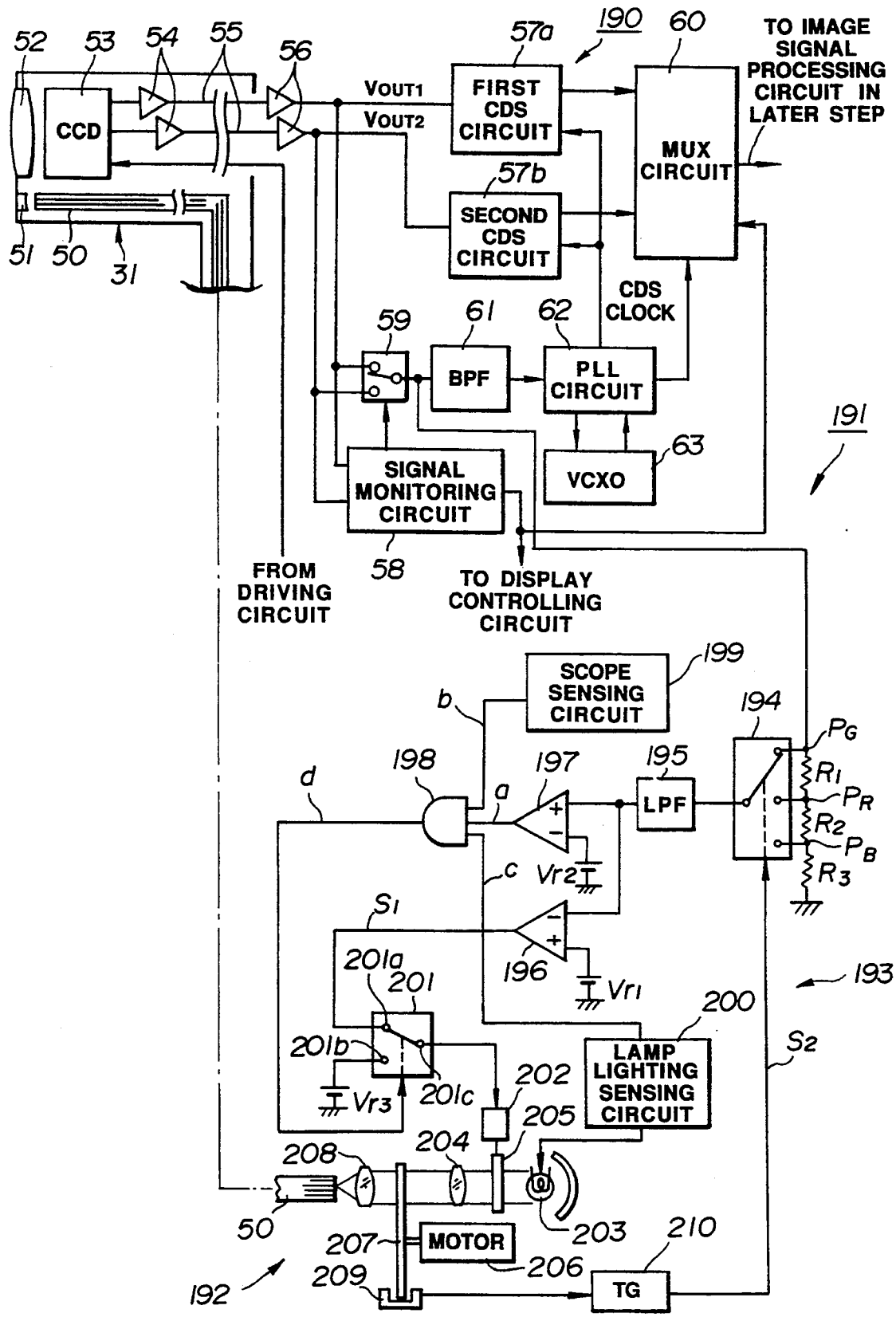
FIGS. 20 to 22 show the ninth embodiment of the present invention.
Figure 21:
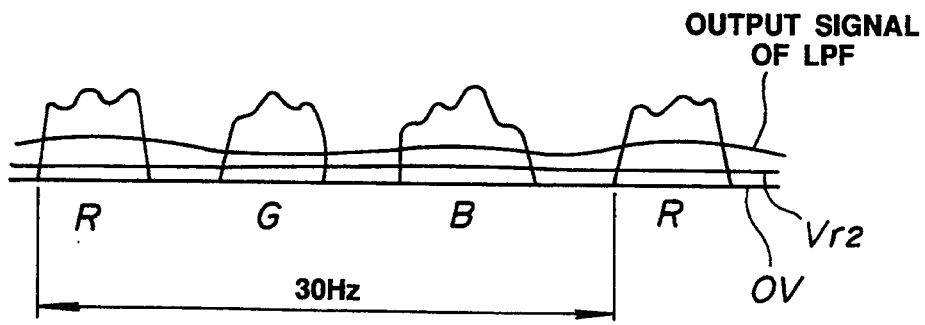
Figure 22:
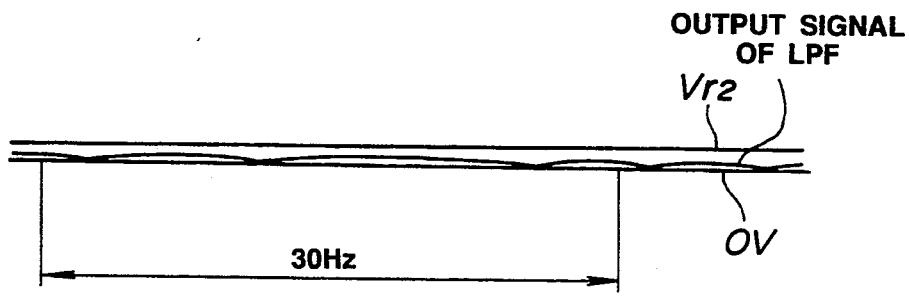

FIGS. 20 to 22 show the ninth embodiment of the present invention.

In the present embodiment, against the electronic endoscope apparatus 30 of the above described first embodiment, even after the signal monitoring circuit 58 senses that the signal read out of one system of the CCD is abnormal due to the deterioration or the like of the CCD 53 and the signal read out of the normal system of the CCD is used, in case the signal level of the signal read out of the normal CCD is below a predetermined value, the light amount of the illuminating light will be decreased to prevent the burn of the light guide fiber bundle 50 by the incidence of an excessive illuminating light or the burn of the affected part of a human body.

As shown in FIG. 20, in the electronic endoscope apparatus 190 of this embodiment, against the image signal processing apparatus 32 in the first embodiment, an image signal processing apparatus 191 having a controlling part 193 for controlling a light source part 192 is connected to the electronic endoscope 31.

The above mentioned controlling part 193 has a series circuit consisting of resistances R1, R2 and R3 and the output end of the selector 59 switched by the signal monitoring circuit 58 is connected to one end of this series circuit. The above mentioned series resistances R1, R2 and R3 are connected at the other ends to the earthing point. The above mentioned one end PG and respective intersections PR and PB are connected to a 3-input selector 194.

The signal levels of the respective PG, PR and PB connected to this selector 194 are set in the order mentioned on the levels conforming to the specific vision sensitivity characteristics of the green light, red light and blue light and can be independently adjusted in the respective three primary color periods.

The output terminal of the above mentioned selector 194 is connected through an LPF 195 to a reverse input terminal of a first comparator 196 and to a non-reverse input terminal of a second comparator 197 as a signal monitoring means judging whether the output signal of the CCD 53 is normal or not. A reference potential Vr1 is connected to a non-reverse input terminal of the first comparator 196, a reference potential Vr2 is connected to a reverse input terminal of the second comparator 197 and the relation between these reference potentials Vr1 and Vr2 is Vr2<<Vr1.

In the first comparator 196, when the average value (luminance signal) of the signals from the selector 194 falls lower than the reference potential Vr1 in the respective three primary color periods, a light adjustment controlling signal S1 will be output.

The output terminal of the above mentioned second comparator 197 is connected to one input terminal of an AND gate 198 and to the other input terminal of this AND gate 198 are connected a scope sensing circuit 199 sensing that the electronic endoscope 31 is connected to an image signal processing apparatus 191 and a lamp lighting sensing circuit sensing that a light source lamp 203 of a light source part 192 is lighted.

The output terminal of the above mentioned first comparator 196 is connected to one input terminal 201a of a switching switch 201 and to the other input terminal 201b is connected a reference potential Vr3. This switching switch 201 has the output signal of the above mentioned AND gate 198 as a switching controlling signal so that, in case the signal from the AND gate 198 is on an H level, the input terminal 201a will be selected but, in case it is on an L level, the input terminal 201b will be selected.

The output terminal 201c of the above mentioned switching switch 201 is connected to a galvanomotor 202 forming a light source part 192. A diaphragm 205 adjusting the light amount of the illuminating light is provided between a light source lamp 203 and a parallel light lens 204 making the illuminating light output from this light source lamp a parallel light and is driven by the above mentioned galvanomotor 202. A light amount attenuating means is formed of the above mentioned galvanomotor 202 and diaphragm 205.

The light having passed through the above mentioned parallel light lens 204 passes through a color separating filter not illustrated provided in the rotary filter disc 207 rotated and driven by the motor 206 and is successively separated into color lights, for example, of red (R), green (G) and blue (B). These color lights are condensed by the condensing lens 208 and are radiated to the incident end surface of the light guide fiber bundle 50.

In the above mentioned rotary filter disc 207 a pulse showing its rotation starting position is detected by a sensor 209. This sensor 209 is connected to the TG 210 and outputs a signal to the TG 210.

The above mentioned TG 210 is connected to the above mentioned selector 194 and controls the switching of the selector 194. That is to say, the TG 210 receiving the pulse detected by the above mentioned sensor 209 is to generate a switching pulse S2 every ⅓ rotation of one rotation period of the rotary filter disc 207 and the position of the above mentioned selector 194 is to be switched and selected by this switching pulse S2.

In the endoscope apparatus 190 formed as mentioned above, the illuminating light output from the light source lamp 203 is made a parallel light by the parallel light lens 204 through the diaphragm 205, is succesively separated into color lights of R, G and B by the rotary filter disc 207 and is radiated to the incident end surface of the light guide fiber bundle 50 by the condensing lens 208.

The illuminating light transmitted through this light guide fiber bundle 50 comes to the tip part of the electronic endoscope 31 and is radiated to the object by the illuminating optical system 51, the reflected light from this object is made to form an image on the imaging surface of the CCD 53 by the objective optical system 52 and the image is converted to an electric signal.

As already explained in the first embodiment, the two signals $V_{out1}$ and $V_{out2}$ read out of the above mentioned CCD 53 are processed by the CDS circuit 57 and MUX circuit 60, are then output to the image signal processing circuit in the later step and are monitored by the signal monitoring circuit 58 as to whether they are normally output or not.

In case both systems of the signals $V_{out1}$ and $V_{out2}$ are normal, one read out signal $V_{out1}$ will be output from the selector 59 and such three RGB primary color signals as are shown in FIG. 21 will be fed to the BPF 61 and series resistances R1, R2 and R3.

By the way, the signal processing for the two signals $V_{out1}$ and $V_{out2}$ read out of the CCD 53 is as already explained in the first embodiment and shall not be explained in the following. Though FIG. 21 shows that the rotary filter disc 207 is rotating at 30 $H_Z$, it may be at others than 30 $H_Z$.

The signal levels of the respective PG, PR and PB of the series resistances R1, R2 and R3 are set to be levels conforming to the specific vision sensitivity characteristics of the green light, red light and blue light in the order mentioned and such output signal as in FIG. 21 is obtained. This output signal is input into the non-reverse input terminal of the second comparator 197 and is compared with the reference potential Vr2 connected to the reverse input terminal. As this reference potential Vr2 is smaller than the output signal of the LPF 195, the signal a which is the output signal from the second comparator 197 will be on an H level and will be input into the AND gate 198.

A signal b on an H level from the scope sensing circuit 199 showing that the electronic endoscope 31 is connected and a signal c on an H level from the lamp lighting sensing circuit 200 showing that the light source lamp 203 is lighted are also input in the AND gate 198 and a signal d which is an output signal becomes on an H level and is fed to the switching switch 201. When the H level signal d is input, the switching switch 201 will select the input terminal 201a.

On the other hand, the output signal of the above mentioned LPF 195 is input into the first comparator 196 at the reverse input terminal and is compared with the reference potential Vr1 connected to the non-reverse input terminal. In case the input signal is larger than the reference potential Vr1, a light adjusting controlling signal S1 will be output on an L level.

This light adjusting controlling signal Si is fed to the switching switch 201 but, as the input terminal 201a side is selected, the L level light adjusting controlling signal S1 will be fed to the galvanomotor 202 which will drive the diaphragm 205 by this signal S1 so that the light amount will decrease. In case the input signal is smaller than the reference potential Vr1, the light adjusting controlling signal S1 will be output as on an H level and, as mentioned above, the galvanomotor 20 will drive the diaphragm 205 so that the light amount will increase. Thus, in case the signals $V_{out1}$ and $V_{out2}$ read out of the CCD 53 are normally output, the light will be adjusted by the first comparator 196.

Here, when one system of the two systems of the read out signals $V_{out1}$ and $V_{out2}$ becomes abnormal due to the deterioration or the like of the CCD 53 and the signal level lowers, by this signal level lowering, the light adjusting controlling signal S1 from the first comparator 196 will be on an H level and will tend to increase the light amount but, before that, the abnormality will be sensed by the signal monitoring circuit 58 and the output signal of the selector 59 will be switched according to the Table 1.

Then the normal system of the signal read out of the CCD is input through the LPF 195 into the first comparator 196 at the reverse input terminal and the second comparator 197 at the non-reverse input terminal and, in the same manner, the light adjustment is controlled by the first comparator 196.

Further, when the two systems of both signals $V_{out1}$ and $V_{out2}$ read out of the CCD 53 become abnormal and the signal level lowers, as shown in FIG. 22, the output of the LPF 195 will become a signal on a level lower than of the reference potential Vr2 and will be input into the first comparator 196 at the reverse input terminal and into the second comparator 197 at the non-reverse input terminal.

In the second comparator 197, as the level of the input signal is lower than the reference potential Vr2, the signal a which is an output signal will become an abnormality sensing signal on an L level and will be input into the AND gate 198. As the signal a is on the L level, the signal d which is an output signal of the AND gate 198 will become on an L level. As the signal d is on the L level, the switching switch 201 will select the input terminal 201b side.

As a result, as the output signal of the LPF 195 has become lower than the reference potential Vr1 (Vr2<<Vr1), the H level light adjusting controlling signal Si output from the first comparator 196 will not be fed to the galvanomotor 202 but the reference potential Vr3 connected to the input terminal 201b will be fed. The reference potential Vr3 is fed to the galvanomoter 202 to fully close the diaphragm 205.

The above mentioned operation is arranged as in Table 2:

TABLE 2

| Signals read out of CCD 53 | Signals | | | | Selection of switching switch | Diaphragm operation |
|---|---|---|---|---|---|---|
| | a | b | c | d | | |
| At least one system is normal | H | H | H | H | 201a | Normal operation |
| Both two systems are abnormal | L | H | H | L | 201b | Fully closed |

By the way, in Table 2, the signal b will be on an H level in case the electronic endoscope 31 is connected to the image signal processing apparatus 191 but will be on an L level in case it is removed. The signal c will be on an H level in case the light source lamp 203 is lighted but will be on an L level in case it is extinguished.

In this embodiment, even if the signal level of either of the signals $V_{out1}$ and $V_{out2}$ read out of the CCD is lowered by such cause as the deterioration of the CCD 53 or the defective connection of the signal cable, the failing system will be switched over to the normal system of the signal read out of the CCD, the image will be processed, the illuminating light will be adjusted and, the same as in the above described respective embodiments, the visual field image in which the endoscope inspection can be continued will be able to be secured.

Further, in case both of the two systems of the signals $V_{out1}$ and $V_{out2}$ read out of the CCD 53 become abnormal and the signal level lowers, by the abnormality sensing signal from the second comparator 197, the signal for increasing the light amount from the first comparator 196 will be prevented, the reference potential Vr3 fully closing the diaphragm 205 will be fed to the galvanomotor 202, the increase of the illuminating light amount will be avoided, the burn within the body cavity of a patient will be prevented, the safety of the patient will be guarded and the burn of the light guide fiber bundle 50 will be able to be prevented.

By the way, in this embodiment, the endoscope apparatus which is of a field sequential system imaging system having a rotary filter has been described but, in the case of a color mosaic type endoscope apparatus, when the switching controlling signal S2 output to the selector 194 from the TG 210 is switched over to a field or frame, the same effects will be able to be obtained.

Figure 24:
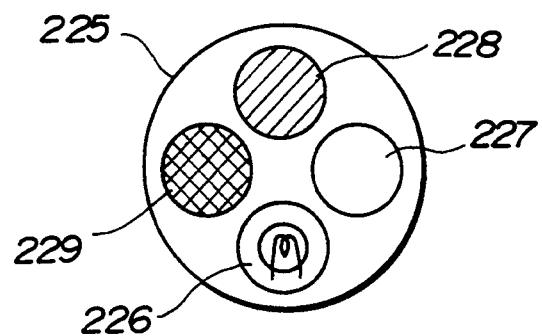
FIGS. 23 and 24 show the tenth embodiment of the present invention.
Figure 23:
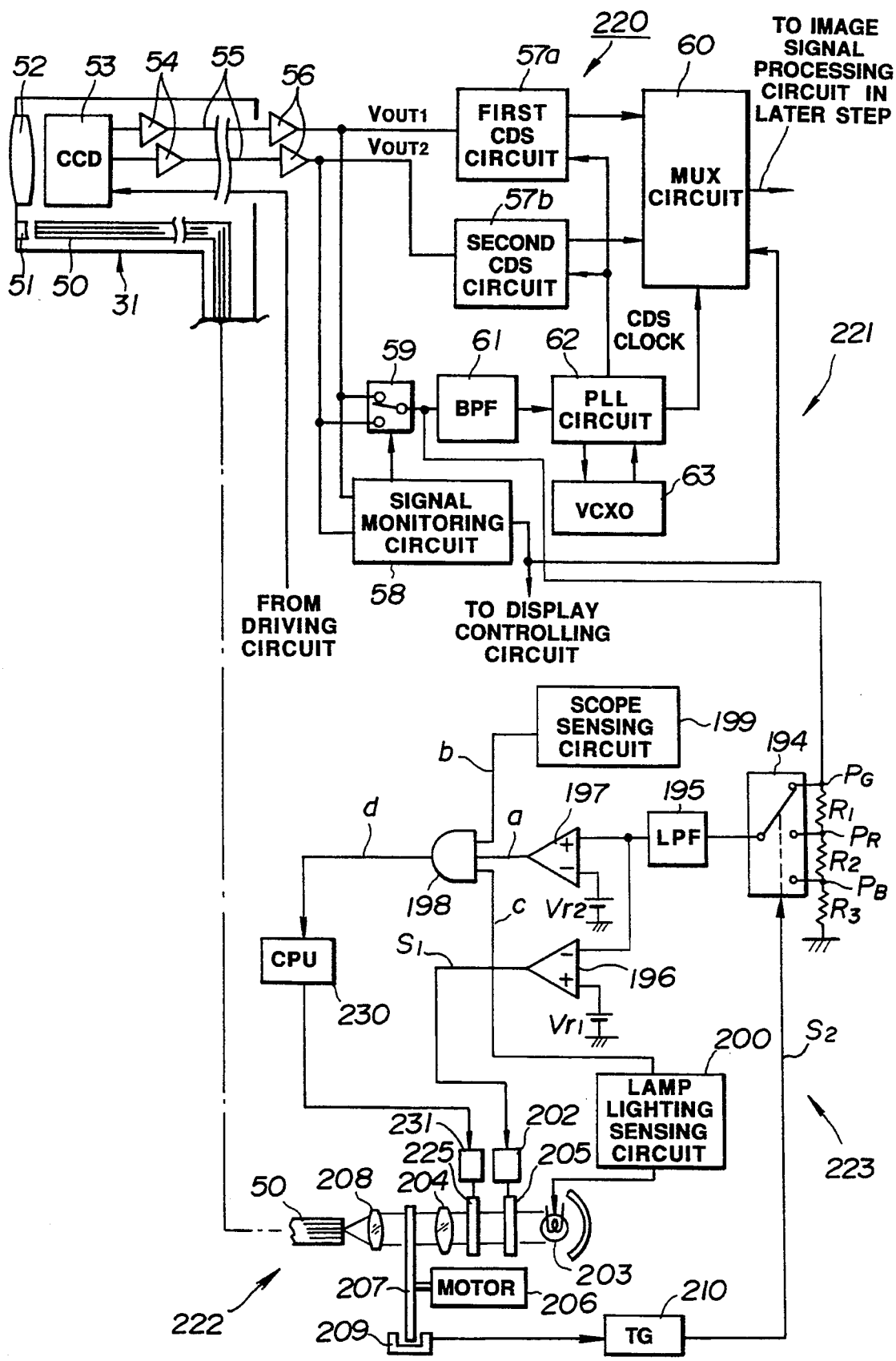

FIGS. 23 and 24 show the tenth embodiment of the present invention.

In this embodiment, against the above described ninth embodiment, a turret plate 225 is provided on the light path connecting the light source lamp 203 and the incident end surface of the light guide fiber bundle 50.

As shown in FIG. 24, this turret plate 225 is disc-like and is provided peripherally with a halogen lamp 226, aperture 227, light shielding part 228 and mesh filter 229.

In case the light source lamp 203 fails, the above mentioned halogen lamp 226 will be inserted in the light path and will output an illuminating light. In the case of an ordinary illumination, the aperture 227 will be positioned in the light path so as to pass the illuminating light.

The mesh filter 229 is inserted in the light path to reduce the illuminating light. In case both signals $V_{out1}$ and $V_{out2}$ read out of the CCD 53 become abnormal, the light shielding part 228 will be inserted into the light path to shield the illuminating light.

As shown in FIG. 23, the above mentioned turret plate 225 is to be driven by a turret plate driving motor 231 and further this turret plate driving motor 231 is connected to a CPU 230 to control the rotation.

The above mentioned CPU 230 is connected to the output terminal of the three-input AND gate described in the ninth embodiment to judge whether the signal from the CCD 53 is normal or not. The other formations are the same as in the ninth embodiment.

In this tenth embodiment, in case both of the two signals $V_{out1}$ and $V_{out2}$ read out of the CCD 53 are abnormal, the same as in the ninth embodiment, by the abnormality sensing signal from the second comparator 197, the signal d output from the AND gate 198 will be on an L level and will be input into the CPU 230. When the L level signal d is input, the CPU 230 will drive the turret plate driving motor 231 so that the illuminating light output from the light source lamp 203 may be shielded by the light shielding part 228.

By the way, not only the light shielding part 228 but also the mesh filter 229 and emergency halogen lamp 226 may be inserted in the light path to reduce the light amount radiated to the light guide fiber bundle 50.

Also, the CPU 230 may make a display for making a danger known, for example, on a monitor picture by taking in an abnormality signal to guard the safety of patients.

The above is arranged and shown in Table 3:

TABLE 3

| Signals read out of CCD 53 | Signals | | | | |
|---|---|---|---|---|---|
| | a | b | c | d | Turret plate |
| At least one system is normal | H | H | H | H | Aperture 227 |
| Both of two systems are abnormal | L | H | H | L | Any one of light shielding part 228, mesh filter 229 and halogen lamp 226 is selected |

The other operations and effects are the same as in the ninth embodiment.

Figure 25:
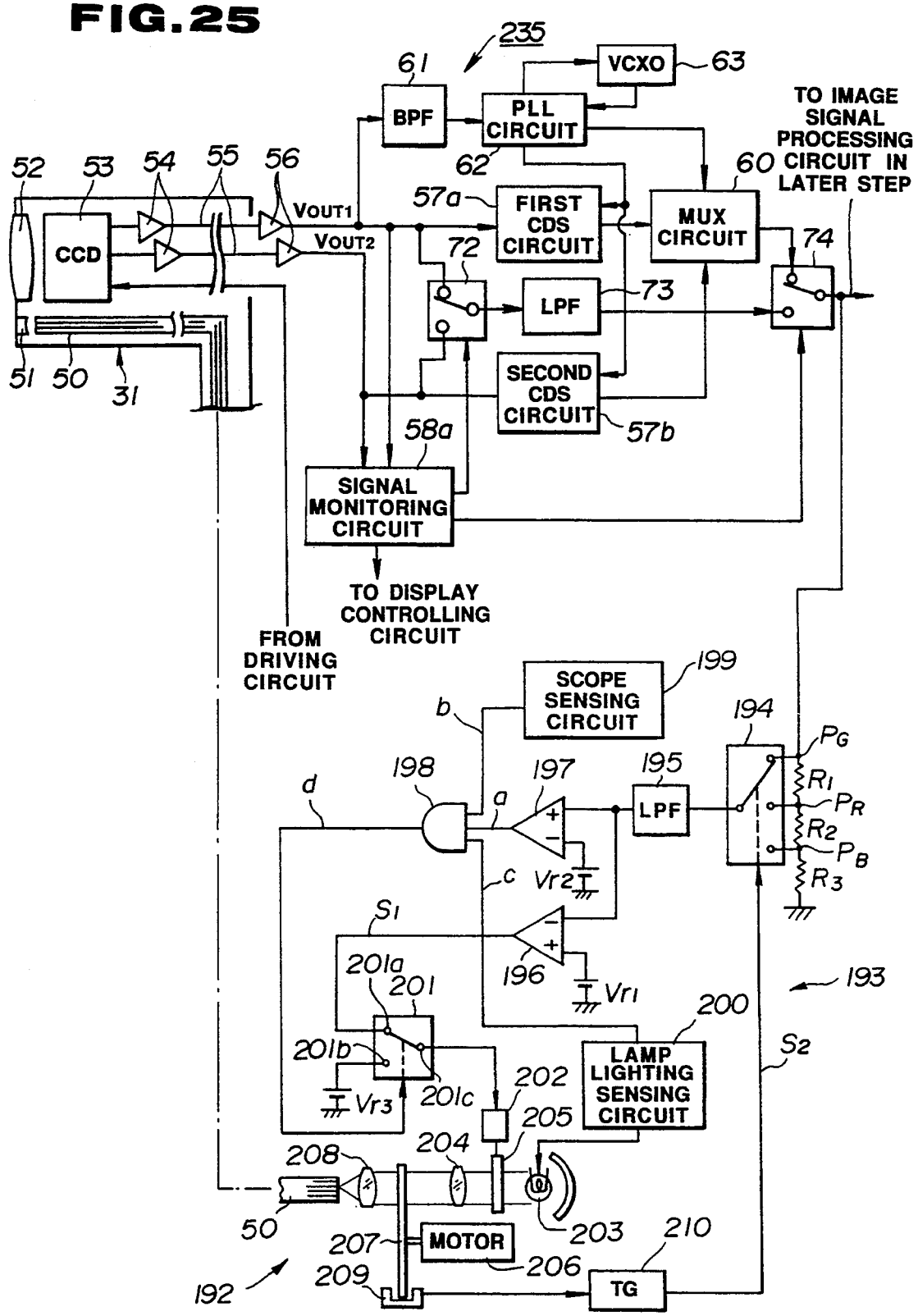
FIG. 25 shows the 11th embodiment of the present invention and is a formation diagram of an electronic endoscope apparatus.

FIG. 25 shows the 11th embodiment of the present invention.

In this embodiment, the circuit formation for processing images is made the formation of the second embodiment, whereas the circuit formation for processing images in the above described ninth embodiment is based on the first embodiment.

As shown in FIG. 25, in the electronic endoscope apparatus 235 of this 11th embodiment, the output end of the second selector 74 switched by the signal processing circuit 58a is connected to one end of the series circuit consisting of R1, R2 and R3 so that the output signal of the CCD 53 may be fed to the controlling part 193 and the light source part may be controlled. The formations and operations of the light source part 192 and controlling part 193 are the same as in the ninth embodiment.

In this embodiment, in case the signal level of either of the signals $V_{out1}$ and $V_{out2}$ is lowered by the deterioration of the CCD 53 or the defective connection of the signal cable, the failing signal will be switched over to the normal system of the signal read out of the CCD, the visual field image in which the endoscope inspection can be continued will be immediately obtained without disturbing the image and further, even in case both of the two systems of the read out signals $V_{out1}$ and $V_{out2}$ become abnormal, the increase of the illuminating light amount will be avoided, the burn within the body cavity of a patient will be prevented, the safety of patients will be guarded, the burn of the light guide fiber bundle 50 will be able to be prevented and therefore a safe and smooth endoscope inspection will be able to be always made.

FIGS. 26 to 31 show modifications of the ninth, tenth and 11th embodiments.

Figure 26:
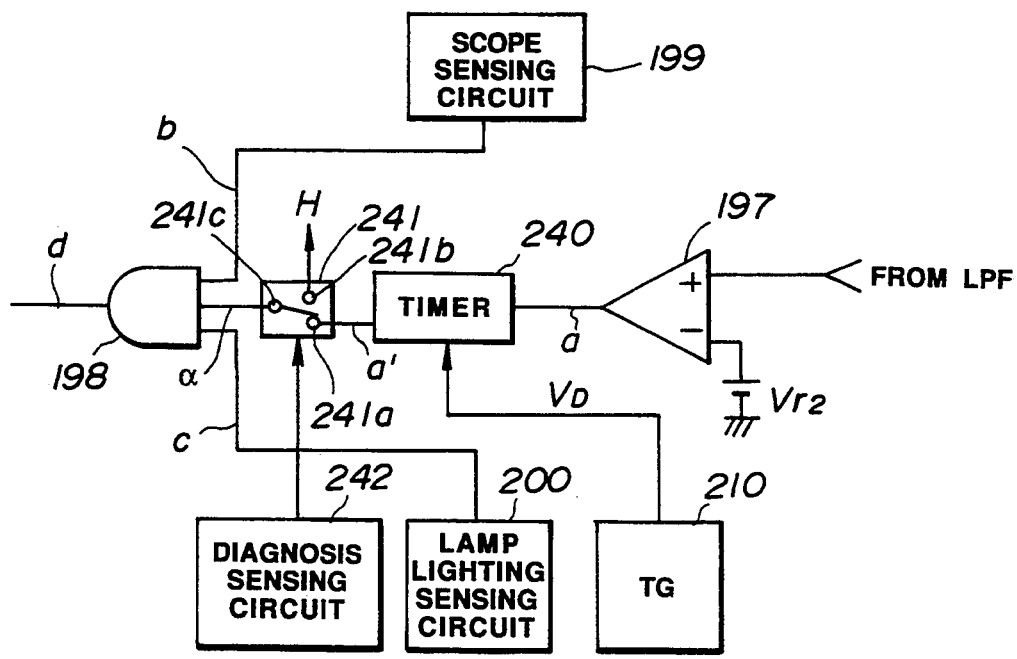
FIGS. 26 to 31 show modifications of the ninth, tenth and 11th embodiments.

In FIG. 26, a timer 240 is connected to the output end of the second comparator 197 in the above described ninth, tenth and 11th embodiments so as to be a signal monitoring means having a time delaying device in the case of detecting an abnormality to prevent the diaphragm 205 from being fully closed for a signal of a minimum level by the object.

That is to say, as shown in FIG. 26, the LPF 195 is connected to the non-reverse input terminal of the second comparator 197 and the reference potential Vr2 is connected to the reverse input terminal the same as in the seventh and eighth embodiments. The output terminal of the second comparator 197 is connected to the timer 240 which is further connected to one input terminal 241a of the switching switch 241. The other input terminal 241b of the switching switch 241 is always on an H level. Also, the output terminal 241c of the switching switch 241 is connected to the input terminal of the three-input AND gate 198 to the other input terminal of which are connected the scope sensing circuit 199 and the lamp lighting sensing circuit 200 the same as in the seventh and eighth embodiments.

The above mentioned switching switch 241 is controlled in switching by the controlling signal from the diagnosis sensing circuit 242. In the diagnosis sensing circuit 242, whether a diagnosis is being made or not is judged by any one or a combination of some of such operations during the diagnosis as, for example, of bending the bendable part 38 of the electronic endoscope 31, feeding air and water and freezing or releasing and, in case it is judged that a diagnosis is being made, the above mentioned switching switch 241 will be switched over to the timer 240 side terminal 241a but, in case a diagnosis is not being made, the above mentioned switching switch 241 will be switched over to the terminal 241b to make the signal a which is an output signal on an H level.

Figure 27:
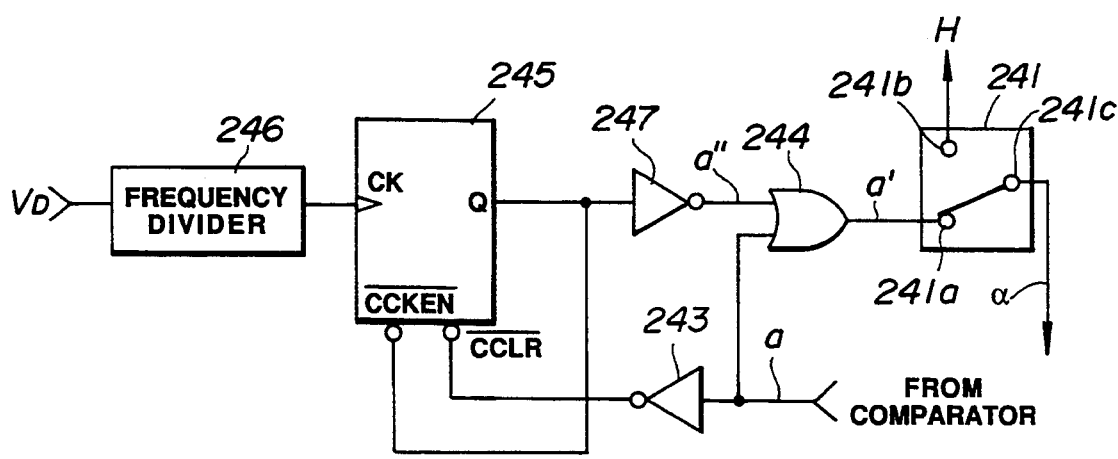
Figure 28:
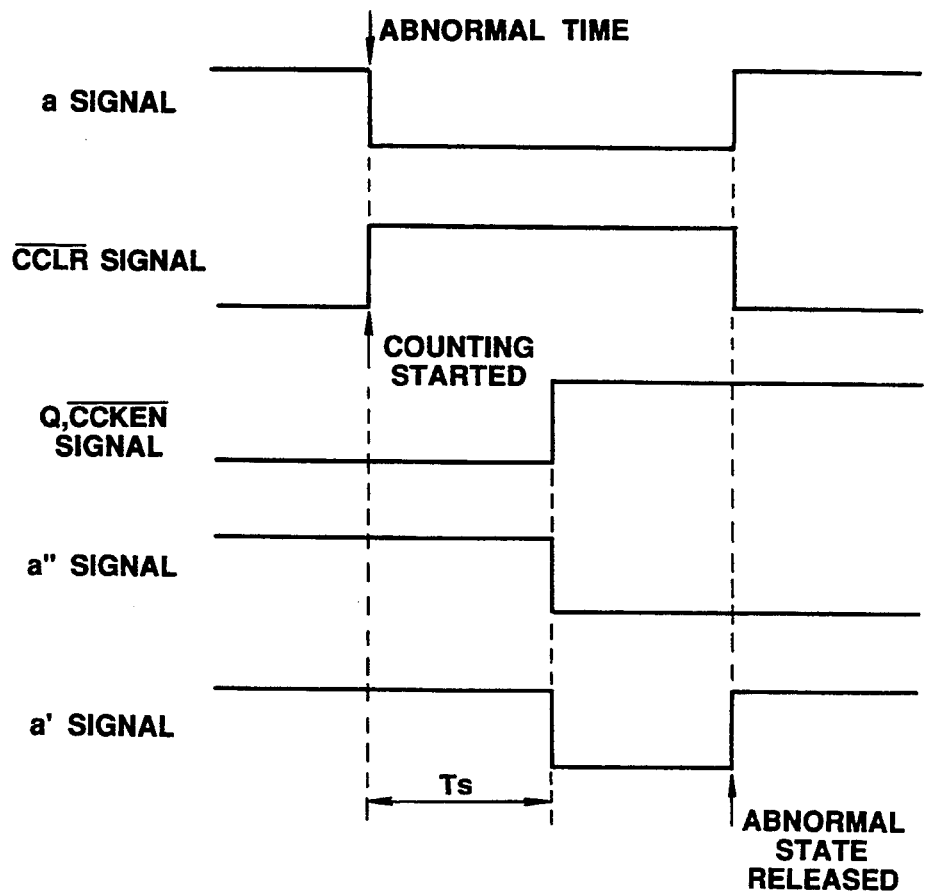

The operation of the timer 240 shall be explained in the following by using FIGS. 27 and 28.

In case the signal from the CCD 53 is abnormal, the signal a from the second comparator 197 will be on an L level, will be input into the inverter 243 and will be input into the OR gate 244. The signal a is inverted by the inverter 243 and this inverted signal is input into the $\overline{CCLR}$ terminal of the counter 245.

The signal obtained by dividing the frequency of the vertical synchronizing signal VD from the TG 210 has been input in the CK terminal of the above mentioned counter 245. Counting is started by making this signal a clock of the counter 245. After counting for the TS time, an H level signal from the output terminal Q is input into the $\overline{CCKEN}$ terminal and inverter 247. At the $\overline{CCKEN}$ terminal, this signal is disabled by being input and the output signal from the output terminal Q is held as it is on the H level.

Therefore, the signal a" of the inverter 247 becomes an abnormality sensing signal on an L level as delayed by the TS time from the time point (when the L level signal is input into the OR gate 244) when it becomes abnormal. The L level signal a" has a logic sum taken by the signal a and OR gate 244 and the L level signal a' is input into the AND gate 198 through the terminal 241a of the switching switch 241.

Here, in case, before the counter 245 counts for the TS time, a signal even a little larger than the reference potential Vr2 is input into the second comparator 197 and the state that the signal from the CCD 53 is abnormal does not continue for a predetermined time, the signal a will be on an H level, the signal a' of the OR gate 244 will be on an H level and the abnormal state will be released.

As a time is set until an abnormality is judged by providing the timer 240, even in case a signal on a minimum level is input into the second comparator 197, the diaphragm 205 will not operate and the minimum level signal will be able to be prevented from being judged by mistake to be "abnormal".

In the switching switch 241, in case it is judged by the diagnosis sensing circuit that a diagnosis is being made, the input terminal 241b side will be selected and the H level signal will be input into the AND gate 198 and, even in case the signal from the second comparator 197 is on an L level, it will not be judged to be abnormal.

Figure 29:
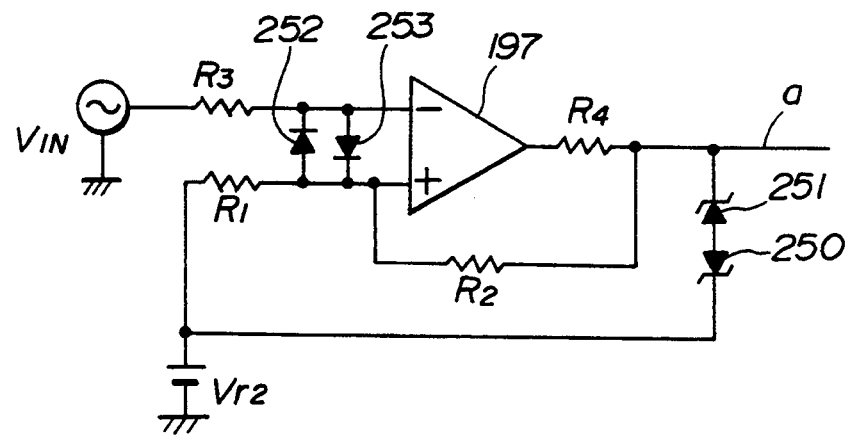

In order to prevent a misoperation by a signal containing a noise, as shown in FIG. 29, the second comparator 197 may be made a Schmitt trigger circuit.

An input signal $V_{IN}$ containing a noise is input into the second comparator 197 at the reverse input terminal and one end of the resistances R1 and R2 is connected to the non-reverse input terminal. The other end of the resistance R1 is connected to the reference potential Vr2 and also to the cathode of the Zener diode 250. The anode of this Zener diode 250 is connected to the anode of the Zener diode 251. Further, the cathode of this Zener diode 251 is connected to the output side of the second comparator 197.

Also, the non-reverse input terminal and reverse input terminal of the second comparator 197 are connected by diodes 252 and 253 connected in parallel so as to be of polarities in the directions reverse to each other. The output terminal of the second comparator 197 is connected to one end of the resistance R4. The other end of this resistance R4 is connected to the other end of the above mentioned resistance R2 and to the cathode of the above mentioned Zener diode 250.

Figure 30:
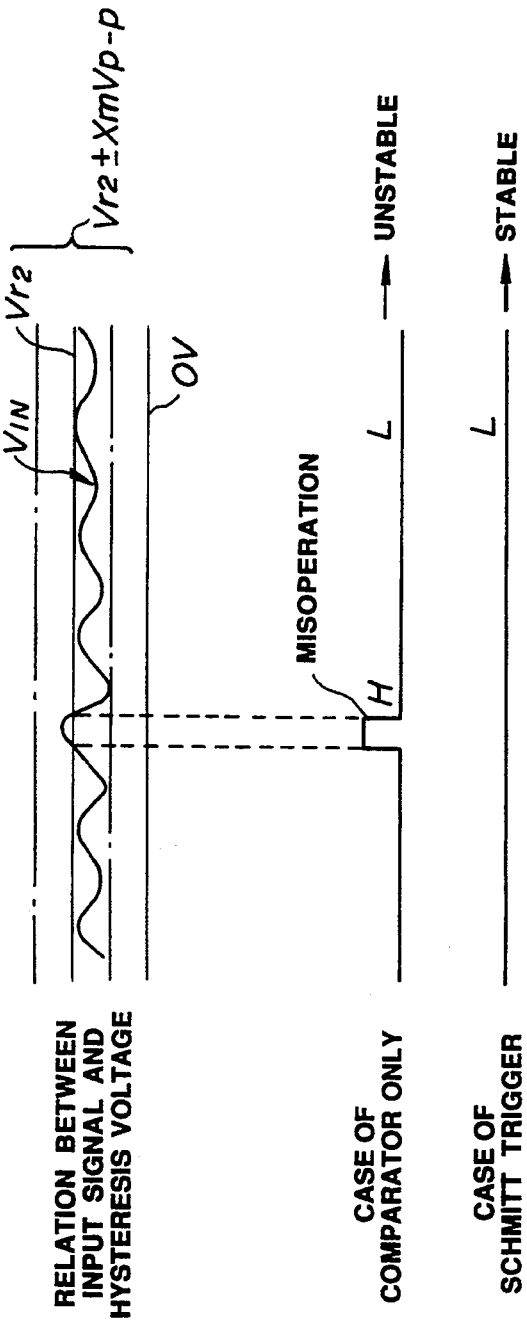

As shown in FIG. 30, in case the second comparator 197 only is for the input signal $V_{IN}$ containing a noise, the noise component will meet the reference potential Vr2, will produce a misoperation and will be unstable but, when the second comparator 197 is made a Schmitt trigger circuit, a hysteresis voltage $\chi$ mVP-P set by the resistances R1 and R2 will be obtained, therefore no misoperation will be produced even against the input signal $V_{IN}$ containing a noise and a stable circuit will be able to be made.

Figure 31:
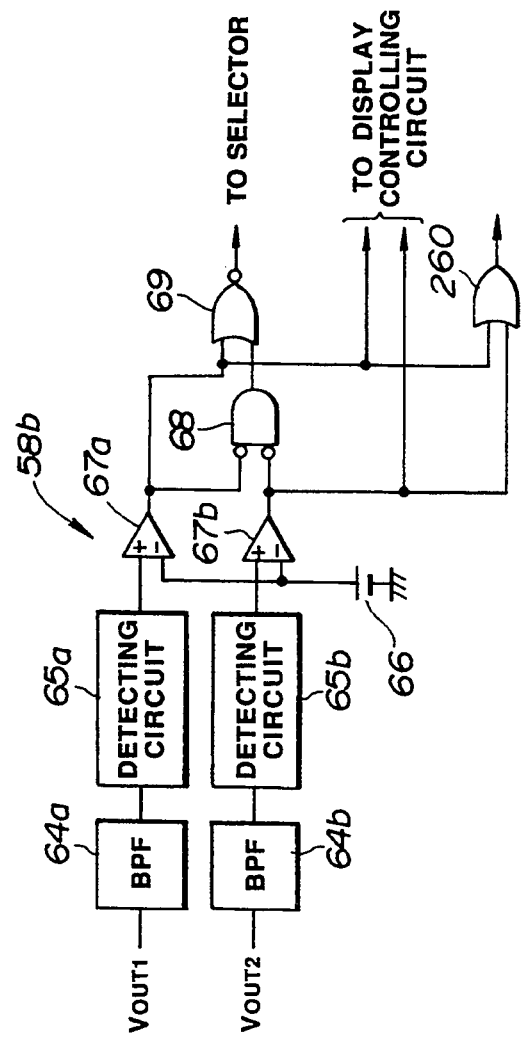

Further, as shown in FIG. 31, the signal monitoring circuit 58 in the ninth, tenth and 11th embodiments may be made a signal monitoring circuit 58b wherein, in addition to the formation shown in FIG. 7, the respective output terminals of the comparators 67a and 67b are connected to the input terminal of the OR gate 260 so that the second comparator 197 may be omitted. The output terminal of the above mentioned OR gate may be connected to the input terminal of the AND gate 198 instead of the second comparator so that the signal sensing that both of the two signals $V_{out1}$ and $V_{out2}$ read out of the CCD 53 are abnormal may be input into the AND gate.

In the above described respective embodiments, the signal read out of the solid state imaging device provided in the electronic endoscope is monitored but it is needless to say that the present invention can be applied also to the solid state imaging device provided in such imaging means as an externally fitted camera fitted to the eyepiece part of an electronic endoscope.

It is apparent that, in this invention, working modes different in a wide range can be formed on the basis of this invention without deviating from the spirit and scope of the invention. This invention is not restricted by its specific working modes except being limited by the appended claims.

What is claimed is:

1. An electronic endoscope apparatus comprising:
    an imaging means for outputting a plurality of systems of signals from at least one solid state imaging device, said systems of signals including a first signal and a second signal;
    a plurality of signal transmitting means for transmitting said plurality of systems of signals output from said at least one solid state imaging device of said imaging means;
    a signal processing means for processing in corresponding processing modes the respective signals transmitted by said plurality of signal transmitting means, wherein said signal processing means comprises at least one pair of first and second correlated double sampling circuits corresponding to the respective first and second signals of said plurality of systems of signals;
    a signal monitoring means for judging whether the respective first and second signals transmitted by said plurality of signal transmitting means are normal or not and outputting a signal for changing the processing mode of said signal processing means on the basis of the judged result;
    wherein said signal processing means further comprises:
        a signal selecting circuit selecting one of said plurality of systems of signals in response to the output from said signal monitoring means;
        a carrier extracting circuit extracting a carrier component from the output signal of said signal selecting circuit;
        a sampling clock producing circuit producing a sampling clock of said plurality of correlated double sampling circuits by the output signal of said carrier extracting circuit; and
        a synthesizing circuit synthesizing the output signals of said plurality of correlated double sampling circuits on the basis of the output of said signal monitoring means.

2. An electronic endoscope apparatus comprising:
    an imaging means for outputting a plurality of systems of signals from at least one solid state imaging device said systems of signals including a first signal and a second signal;
    a plurality of signal transmitting means for transmitting said plurality of systems of signals output from said at least one solid state imaging device of said imaging means;
    a signal processing means for processing in corresponding processing modes the respective signals transmitted by said plurality of signal transmitting means, wherein said signal processing means comprises at least one pair of first and second correlated double sampling circuits corresponding to the respective first and second signals of said plurality of systems of signals;

a signal monitoring means for judging whether the respective first and second signals transmitted by said plurality of signal transmitting means are normal or not and outputting a signal for changing the processing mode of said signal processing means on the basis of the judged result;

wherein said signal processing means further comprises:

a first signal selecting circuit selecting one of said plurality of systems of signals in response to the output from said signal monitoring means;

a carrier removing circuit removing a carrier component from the output signal of said signal selecting circuit;

a synthesizing circuit synthesizing the output signals of said plurality of correlated double sampling circuits on the basis of the output of said signal monitoring means; and a second signal selecting circuit selecting the output signal of said synthesizing circuit and the output signal of said carrier removing circuit on the basis of the output of said signal monitoring means.

3. An electronic endoscope apparatus comprising:

an imaging means for outputting a plurality of systems of signals from at least one solid state imaging device, said systems of signals including a first signal and a second signal;

a plurality of signal transmitting means for transmitting said plurality of systems of signals output from said at least one solid state imaging device of said imaging means;

a signal processing means for processing in corresponding processing modes the respective signals transmitted by said plurality of signal transmitting means, wherein said signal processing means comprises at least one pair of first and second correlated double sampling circuits corresponding to the respective first and second signals of said plurality of systems of signals;

a signal monitoring means for judging whether the respective first and second signals transmitted by said plurality of signal transmitting means are normal or not and outputting a signal for changing the processing mode of said signal processing means on the basis of the judged result;

wherein said signal processing means further comprises:

a first signal processing circuit and a second signal processing circuit, said first signal processing circuit comprising:

said plurality of correlated double sampling circuits corresponding to the respective signals of said plurality of systems of signals;

a signal selecting circuit selecting one of said plurality of systems of signals in response to the output from said signal monitoring means;

a carrier extracting circuit extracting a carrier component from the output signal of said signal selecting circuit;

a sampling clock producing circuit producing a sampling clock of said plurality of correlated double sampling circuits by the output signal of said carrier extracting circuit; and a synthesizing circuit synthesizing the output signals of said plurality of correlated double sampling circuits on the basis of the output of said signal monitoring means; and said second signal processing circuit comprising:

a synchronizing detecting circuit synchronizing and detecting the output signal from the synthesizing circuit in said first signal processing circuit and extracting a color difference signal; and a synchronizing detecting clock producing circuit producing a synchronizing detecting clock of said synchronizing detecting circuit on the basis of the output of said signal monitoring means.

4. An electronic endoscope apparatus comprising:

an imaging means for outputting a plurality of systems of signals from at least one solid state imaging device, said systems of signals including a first signal and a second signal;

a plurality of signal transmitting means for transmitting said plurality of systems of signals output from said at least one solid state imaging device of said imaging means;

a signal processing means for processing in corresponding processing modes the respective signals transmitted by said plurality of signal transmitting means, wherein said signal processing means comprises at least one pair of first and second correlated double sampling circuits corresponding to the respective first and second signals of said plurality of systems of signals;

a signal monitoring means for judging whether the respective first and second signals transmitted by said plurality of signal transmitting means are normal or not and outputting a signal for changing the processing mode of said signal processing means on the basis of the judged result;

wherein said signal processing means further comprises:

a first signal processing circuit and a second signal processing circuit, said first signal processing circuit comprising:

said plurality of correlated double sampling circuits corresponding to the respective signals of said plurality of systems of signals;

a first signal selecting circuit selecting one of said plurality of systems of signals in response to the output from said signal monitoring means;

a carrier removing circuit removing a carrier component from the output signal of said first signal selecting circuit;

a synthesizing circuit synthesizing the output signals of said plurality of correlated double sampling circuits on the basis of the output of said signal monitoring means; and a second signal selecting circuit selecting the output signal of said synthesizing circuit and the output signal of said carrier removing circuit on the basis of the output of said signal monitoring means; and said second signal processing circuit comprising:

a synchronizing detecting circuit synchronizing and detecting the output signal from the second signal selecting circuit in said first signal processing circuit and extracting a color difference signal; and a synchronizing detecting clock producing circuit producing a synchronizing detecting clock of said synchronizing detecting circuit on the basis of the output of said signal monitoring means.

* * * * *